(12) United States Patent
Singh et al.

(10) Patent No.: US 6,406,667 B1
(45) Date of Patent: Jun. 18, 2002

(54) CHEMILUMINESCENT COMPOSITIONS FOR USE IN DETECTION OF MULTIPLE ANALYTES

(75) Inventors: Sharat Singh, San Jose; Edwin F. Ullman, Atherton, both of CA (US)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 09/333,237

(22) Filed: Jun. 15, 1999

Related U.S. Application Data

(63) Continuation of application No. 09/025,624, filed on Feb. 18, 1998, now abandoned.

(51) Int. Cl.$^7$ .............................................. G01N 21/64
(52) U.S. Cl. ........................ 422/52; 422/61; 436/534; 436/172
(58) Field of Search ................... 422/61, 52; 436/533, 436/534, 535, 537, 172

(56) References Cited

U.S. PATENT DOCUMENTS

| | | | |
|---|---|---|---|
| 4,193,983 A | 3/1980 | Ullman et al. | |
| 4,666,862 A | 5/1987 | Chan | |
| 4,745,075 A | 5/1988 | Hadfield et al. | |
| 4,868,103 A | * 9/1989 | Stavrianopoulos et al. | 435/5 |
| 4,891,324 A | 1/1990 | Pease et al. | |
| 5,017,473 A | 5/1991 | Wagner | |
| 5,326,692 A | 7/1994 | Brinkley et al. | |
| 5,340,716 A | 8/1994 | Ullman et al. | |
| 5,512,493 A | 4/1996 | Mathis et al. | |
| 5,516,636 A | * 5/1996 | McCapra | 435/6 |
| 5,567,627 A | 10/1996 | Lehnen | |
| 5,573,909 A | 11/1996 | Singer et al. | |
| 5,618,732 A | * 4/1997 | Pease et al. | 436/172 |
| 5,656,207 A | 8/1997 | Woodhead et al. | |
| 5,672,475 A | 9/1997 | Lee et al. | |
| 5,672,478 A | * 9/1997 | Singh et al. | 435/4 |
| 5,674,698 A | 10/1997 | Zarling et al. | |
| 5,709,994 A | * 1/1998 | Pease et al. | 252/582 |
| 5,716,855 A | 2/1998 | Lerner et al. | |
| 5,807,675 A | * 9/1998 | Davalian et al. | 435/6 |

FOREIGN PATENT DOCUMENTS

| | | |
|---|---|---|
| EP | 345776 | 12/1989 |
| EP | 515194 A2 | 11/1992 |
| WO | 94/03812 | 2/1994 |
| WO | WO 97/41442 | 6/1997 |

\* cited by examiner

Primary Examiner—Jeffrey Snay
(74) Attorney, Agent, or Firm—Theodore J. Leitereg

(57) ABSTRACT

Methods, compositions and kits are disclosed. The methods are directed to determining the presence or relative amounts of two or more components in a medium. A combination is provided comprising a medium suspected of containing the components and a label reagent for each of the components. The label reagent comprises a chemiluminescent composition that is activated by electromagnetic radiation. A first specific binding pair (sbp) member may be associated with the reagent depending on the components to be determined. Luminescence emitted by each of the chemiluminescent compositions upon activation is differentially detectable. Where a first sbp member is employed, it is capable of binding to the component or to a second sbp member to form a complex related to the amount of the component. At least one of the chemiluminescent compositions comprises a fluorescent energy acceptor. After the above are combined, the chemiluminescent compositions are activated. The amount of luminescence generated by each of the chemiluminescent compositions is detected and related to the amount of each of the components in the medium.

12 Claims, No Drawings

SEQUENCE LISTING

<160> NUMBER OF SEQ ID NOS: 8

<210> SEQ ID NO 1
<211> LENGTH: 45
<212> TYPE: DNA
<213> ORGANISM: Artificial Sequence
<220> FEATURE:
<223> OTHER INFORMATION: oligonucleotide probe for binding to HIV target and reference sequences

<400> SEQUENCE: 1 ttttttttttt ttttttttttt tgttaaaaga gaccatcaat gagga          45

<210> SEQ ID NO 2
<211> LENGTH: 38
<212> TYPE: DNA
<213> ORGANISM: Artificial Sequence
<220> FEATURE:
<223> OTHER INFORMATION: oligonucleotide probe for binding to HIV target sequence

<400> SEQUENCE: 2
tacttactta cttacttact gctgcagaat gggataga          38

<210> SEQ ID NO 3
<211> LENGTH: 38
<212> TYPE: DNA
<213> ORGANISM: Artificial Sequence
<220> FEATURE:
<223> OTHER INFORMATION: oligonucleotide probe for binding to HIV reference sequence

<400> SEQUENCE: 3
gatgacagtc gcatgcagct atctatctat ctatctat          38

<210> SEQ ID NO 4
<211> LENGTH: 24
<212> TYPE: DNA
<213> ORGANISM: Artificial Sequence
<220> FEATURE:
<223> OTHER INFORMATION: detection probe bound to sensitizer particle -continued

```
<400> SEQUENCE: 4
aaaaaaaaaa aaaaaaaaaa aaaa                                              24

<210> SEQ ID NO 5
<211> LENGTH: 24
<212> TYPE: DNA
<213> ORGANISM: Artificial Sequence
<220> FEATURE:
<223> OTHER INFORMATION: detection probe bound to chemiluminescent
      particle

<400> SEQUENCE: 5
atagatagat agatagatag atag                                              24

<210> SEQ ID NO 6
<211> LENGTH: 24
<212> TYPE: DNA
<213> ORGANISM: Artificial Sequence
<220> FEATURE:
<223> OTHER INFORMATION: detection probe bound to chemiluminescent
      particle

<400> SEQUENCE: 6
atgaatgaat gaatgaatga atga                                              24

<210> SEQ ID NO 7
<211> LENGTH: 38
<212> TYPE: DNA
<213> ORGANISM: Artificial Sequence
<220> FEATURE:
<221> NAME/KEY: misc_binding
<222> LOCATION: (1)...(38)
<223> OTHER INFORMATION: Synthetic DNA Probe

<400> SEQUENCE: 7
gctgcagaat gggatagata cttacttact tacttact                               38

<210> SEQ ID NO 8
<211> LENGTH: 39
<212> TYPE: DNA
<213> ORGANISM: Artificial Sequence
<220> FEATURE:
<221> NAME/KEY: misc_binding
<222> LOCATION: (1)...(39)
<223> OTHER INFORMATION: Synthetic DNA Probe

<400> SEQUENCE: 8
gctgcagaca gtgtagatac tatctatcta tctatctat                              39
```

CHEMILUMINESCENT COMPOSITIONS FOR USE IN DETECTION OF MULTIPLE ANALYTES

CROSS REFERENCE TO RELATED APPLICATION

This application is a continuation of U.S. patent application Ser. No. 09/025,624 filed Feb. 18, 1998, now abandoned, the disclosure of herein by reference.

BACKGROUND OF THE INVENTION

1. Field of the Invention

This invention relates to methods, compositions and kits for detecting a number of different components in a single test medium.

The clinical diagnostic field has seen a broad expansion in recent years, both as to the variety of materials of interest that may be readily and accurately determined, as well as the methods for the determination. Convenient, reliable and non-hazardous means for detecting the presence of low concentrations of materials in liquids is desired. In clinical chemistry these materials may be present in body fluids in concentrations below $10^{-12}$ molar. The difficulty of detecting low concentrations of these materials is enhanced by the relatively small sample sizes that can be utilized.

The need to determine many analytes in blood and other biological fluids has become increasingly apparent in many branches of medicine. In endocrinology the knowledge of plasma concentration of a number of different hormones is often required to resolve a diagnostic problem or a panel of markers for a given diagnosis where the ratios could assist in determining disease progression. An even more pressing need is evident in other areas such as allergy testing, the screening of transfused blood for viral contamination or genetic diagnosis.

In other assays such as nucleic acid hybridization assays, there is need to detect and quantify specific target and positive control sequence in a single tube without time consuming separations and transfer steps. In principle internal controls will eliminate the need for a standard curve. Amplification and detection in a single tube without opening the tube also overcomes contamination problems. In mutation analysis, the ability to measure two or more variants in a single tube would allow one to monitor quantitatively the appearance of mutant populations.

Most multi-analyte assays are heterogeneous, have poor sensitivity and poor dynamic range (2 to 100 fold difference in concentration of the analytes is determined) and some require the use of sophisticated instrumentation. A homogeneous assay that has higher sensitivity, large dynamic range ($10^3$ to $10^4$-fold difference in analyte concentration), and fewer and more stable reagents would increase the simplicity and reliability or multianalyte assays.

Luminescent compounds, such as fluorescent compounds and chemiluminescent compounds, find wide application in the assay field because of their ability to emit light. For this reason, luminescers have been utilized as labels in assays such as nucleic acid assays and immunoassays. For example, a member of a specific binding pair is conjugated to a luminescer and various protocols are employed. The luminescer conjugate can be partitioned between a solid phase and a liquid phase in relation to the amount of analyte in a sample suspected of containing the analyte. By measuring the luminescence of either of the phases, one can relate the level of luminescence observed to a concentration of the analyte in the sample.

Particles, such as liposomes and erythrocyte ghosts, have been utilized as carriers of encapsulated water-soluble materials. For example, liposomes have been employed to encapsulate biologically active material for a variety of uses, such as drug delivery systems wherein a medicament is entrapped during liposome preparation and then administered to the patient to be treated.

Particles, such as latex beads and liposomes, have also been utilized in assays. For example, in homogeneous assays an enzyme may be entrapped in the aqueous phase of a liposome labeled with an antibody or antigen. The liposomes are caused to release the enzyme in the presence of a sample and complement. Antibody or antigen-labeled liposomes, having water soluble fluorescent or non-fluorescent dyes encapsulated within an aqueous phase vesicle or lipid soluble dyes dissolved in the lipid bilayer of a lipid, have also been utilized to assay for analytes capable of entering into an immunochemical reaction with the surface bound antibody or antigen. Detergents have been used to release the dyes from the aqueous phase of the liposomes.

Various labels have been used to produce distinguishable signals in multianalyte assays: (a) two different radioisotope labels, (b) two or more different fluorescent labels, (c) a fluorescent and a chemiluminescent label, (c) different lanthanide chelates where both lifetime and wavelength are measured, (e) an enzyme and an acridinium ester, (f) spatial resolution of different analytes, (g) different enzymes with sequential substrate additions, and (h) different acridinium esters that produce dioxetanones having different lifetimes.

2. Brief Description of the Related Art

U.S. Pat. No. 5,656,207 (Woodhead, et al.) discloses a method for detecting or quantifying multiple analytes using labelling techniques.

U.S. Pat. No. 5,340,716 (Ullman, et al.) describes an assay method utilizing photoactivated chemiluminescent labels.

Photoactivatable chemiluminescent matrices are described in patent application WO 94/03812 (Pease, et at.).

European Patent Application No. 0 515 194 A2 (Ullman, et at.) discloses assay methods utilizing induced luminescence. The references cited therein are incorporated herein by reference including without limitation U.S. Pat. No. 5,017,473 (Wagner), which discloses a homogeneous chemiluminescence immunoassay using a light absorbing material, European Patent Application No. 0,345,776 (McCapra), which discloses specific binding assays that utilize a sensitizer as a label, U.S. Pat. No. 4,193,983 (Ullman, et al.), which discloses labeled liposome particle compositions and immunoassays therewith, U.S. Pat. No. 4,891,324 (Pease, et al.), which describes a particle with luminescer for assays.

SUMMARY OF THE INVENTION

One aspect of the present invention is a method for determining the presence or relative amounts of two or more components in a medium. A combination is provided comprising a medium suspected of containing the components and a label reagent for each of the components. The label reagent comprises a chemiluminescent composition. Luminescence emitted by each of the chemiluminescent compositions is activated by electromagnetic radiation and is differentially detectable. At least one of the chemiluminescent compositions comprises a fluorescent energy acceptor. The chemiluminescent compositions are activated and the amount of luminescence generated by each of the chemiluminescent compositions is detected. The amount of luminescence is related to the amount of each of the components in the medium.

Another aspect of the present invention is a method for determining the presence or relative amounts of two or more components in a medium. A combination is provided comprising a medium suspected of containing the components and a label reagent for each of the components. The label reagent comprises a first specific binding pair (sbp) member associated with a chemiluminescent composition. Luminescence emitted by each of the chemiluminescent compositions activated by electromagnetic radiation and is differentially detectable. The first sbp member is capable of binding to the component or to a second sbp member to form a complex related to the amount of the component. At least one of the chemiluminescent compositions comprises a fluorescent energy acceptor. After the above are combined, the chemiluminescent compositions are activated. The amount of luminescence generated by each of the chemiluminescent compositions is detected and related to the amount of each of the components in the medium.

Another aspect of the present invention is a homogeneous method for determining the presence or relative amounts of two or more components in a medium. A combination is provided comprising a medium suspected of containing the components and a label reagent for each of the components. The label reagent comprises a first specific binding pair (sbp) member associated with a chemiluminescent composition. Each of the chemiluminescent compositions comprises an olefinic compound activatable by singlet oxygen and a fluorescent energy acceptor. Furthermore, each of the chemiluminescent compositions has a different combination of luminescent emission wavelength and rate of decay. The first sbp member is capable of binding to the component or to a second sbp member to form a complex related to the amount of the component. The chemiluminescent compositions are activated with singlet oxygen. The amount of luminescent emission generated by each of the chemiluminescent compositions is detected at a time after activation and at a wavelength corresponding to the rate of decay and wavelength of the luminescent emission. The amount of emission is related to the presence of relative amounts of the components.

Another aspect of the present invention is a homogeneous method for determining the presence or relative amounts of a plurality of components in a medium. A combination is provided comprising a medium suspected of containing the plurality of components, a label reagent for each of the components and a photosensitizer. The label reagents comprise a first specific binding pair (sbp) member associated with a chemiluminescent composition. Each of the chemiluminescent compositions comprises an olefinic compound activatable by singlet oxygen and a fluorescent energy acceptor. Each of the chemiluminescent compositions has a different combination of luminescent emission wavelength and rate of decay. The first sbp member is capable of binding to the component or to a second sbp member to form a complex related to the amount of the component. The medium is irradiated with light, and the amount of luminescent emission generated by each of the chemiluminescent compositions is detected at a time after irradiation and at a wavelength corresponding to the rate of decay and wavelength of the luminescent emission. The amount of the luminescent emission is related to the amount of each of the components in the medium.

Another aspect of the present invention is a kit comprising in packaged combination a plurality of label reagents and a photosensitizer. Each label reagent comprises a chemiluminescent composition associated with a particle and a member of a specific binding pair (sbp). Each of the chemiluminescent compositions comprises an olefinic compound activatable by singlet oxygen and a fluorescent energy acceptor. Each of the chemiluminescent compositions has luminescent emissions of different wavelength.

DESCRIPTION OF THE SPECIFIC EMBODIMENTS

The present invention permits quantitative detection of different analytes in an assay by the use of different chemiluminescent compositions that can be activated by electromagnetic radiation. Certain olefinic compounds such as thioxenes, dihydrooxazines, and dioxenes are known to react with singlet oxygen to form 1,2-dioxetanes that decompose at different rates and with the emission of light. We have found that some fluorescent energy acceptors also accelerate the rate of decay of these compounds and, thus, affect the rate of decay of their chemiluminescent emissions. By the judicious choice of chemiluminescent compositions having different lifetimes and emission maxima, we found that quantitative determination of each of a plurality of compositions can be made even when combined in a single medium.

In the present method quantitatively differentiable chemiluminescent compositions that comprise fluorescent energy acceptors are used as labels in the simultaneous detection of nucleic acids, proteins, and the like. Preferably, the labels used in the present invention are chemiluminescers that have a fluorescent energy acceptor covalently attached or otherwise held in proximity. A particularly attractive approach is to have the chemiluminescent compositions dissolved in a suitable matrix such as a liposome or oil droplet or latex. Preferred chemiluminescers are olefins that are activated by light, usually by reaction with singlet oxygen. Other chemiluminescers that may be used include, for example, stable dioxetanes that can be activated with base or an enzyme, hydrazides such as luminol that are activated with a peroxide, chemiluminescent enzyme substrates such as luciferin, and so forth.

As mentioned above, the compositions of the present invention are most effective when activatable by singlet oxygen. The signals can be deconvoluted by use of lifetime and wavelength measurements, preferably by the simultaneous use of both methods.

Before proceeding further with a description of the specific embodiments of the present invention, a number of terms will be defined and described in detail.

Component—component of interest; the compound or composition to be detected. The component may be an analyte, a reference compound, a control compound, a calibrator, and the like.

Analyte—the analyte is usually comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as a bacterium or a cell bearing a blood group antigen such as A, B, D, etc., or an HLA antigen or the analyte may be a microorganism, e.g., bacterium, fungus, protozoan, or virus.

The polyvalent ligand analytes will normally be poly (amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones. Other polymeric materials of interest are mucopolysaccharides and polysaccharides.

The monoepitopic ligand analytes will generally be from about 100 to 2,000 molecular weight, more usually from 125 to 1,000 molecular weight. The analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The next group of drugs includes steroids, which includes the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g., phenobarbital and secobarbital, diphenylhydantoin, primidone, ethosuximide, and their metabolites.

The next group of drugs is aminoalkylbenzenes, with alkyl of from 2 to 3 carbon atoms, which includes the amphetamines; catecholamines, which includes ephedrine, L-dopa, epinephrine; narceine; papaverine; and metabolites of the above.

The next group of drugs is benzheterocyclics, which include oxazepam, chlorpromazine, tegretol, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs is the hormones such as thyroxine, cortisol, triiodothyronine, testosterone, estradiol, estrone, progestrone, polypeptides such as angiotensin, LHRH, and immunosuppresants such as cyclosporin, FK506, mycophenolic acid, and so forth.

The next group of drugs includes the vitamins such as A, B, e.g. B12, C, D, E and K, folic acid, thiamine.

The next group of drugs is prostaglandins, which differ by the degree and sites of hydroxylation and unsaturation.

The next group of drugs is the tricyclic antidepressants, which include imipramine, dismethylimipramine, amitriptyline, nortriptyline, protriptyline, trimipramine, chlomipramine, doxepine, and desmethyldoxepin, The next group of drugs is the anti-neoplastics, which include methotrexate.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

The analyte may be a molecule found directly in a sample such as biological tissue, including body fluids, from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The biological tissue includes excised tissue from an organ or other body part of a host and body fluids, for example, urine, blood, plasma, serum, saliva, semen, stool, sputum, cerebral spinal fluid, tears, mucus, and the like.

Label reagent—a reagent for use in conducting an assay for multiple components. The reagent comprises a label that is a chemiluminescent composition in accordance with the present invention. The label reagent also comprises a member of a specific binding pair.

Chemiluminescent composition—also referred to herein as a label; a composition that undergoes a detectable change and is differentially detectable with respect to other chemiluminescent compositions used in the present invention. The labels are differentially detectable by virtue of different wavelengths of emission and/or different rates of decay following activation. When differentially detectable by virtue of wavelength alone, the emission wavelength maxima of the respective labels should differ by at least the average width of the emission peaks at half height, preferably, double, more preferably, triple the average width with present day instrumentation. It should be noted that the above parameters could be adjusted as a result of advances in instrumentation. When differentially detectable by virtue of different decay rates alone, the rates should differ by at least a factor of two, preferably a factor of five, more preferably, by at least a factor of ten, again based on present day instrumentation. When differentially detectable by both wavelength and rate of decay, smaller differences in these parameters can provide acceptable differentiation of the labels.

Examples of chemiluminescers, by way of illustration and not limitation, are olefins capable of reacting with singlet oxygen, e.g., to form hydroperoxides or dioxetanes, stable dioxetanes that can be activated with base or an enzyme, acetylenes that can react with singlet oxygen to form diketones, hydrazones or hydrazides that are activated with a peroxide and that can form azo compounds or azo carbonyls such as luminol, chemiluminescent enzyme substrates such as luciferin, aromatic compounds that can form endoperoxides, etc. At least one of the labels includes a fluorescent energy acceptor in close proximity such as by covalent attachment or by incorporation in a matrix with the chemiluminescer. The labels can produce any detectable signal upon reaction with singlet oxygen and subsequent reaction of the initial reaction product. The signal will usually be initiated by and/or detected as electromagnetic radiation and will preferably be luminescence such as chemiluminescence, fluorescence, electroluminescence or phosphorescence.

Olefins capable of reaction with singlet oxygen—a typical reaction of olefins with singlet oxygen is 2+2 addition to form a dioxetane. Suitable olefins usually have no saturated C—H group attached to an olefinic carbon except unreactive bridgehead carbons and will preferably have one or more electrons donating groups directly attached to the olefinic carbon or in conjugation with the olefin. Dioxetanes can dissociate spontaneously or by heating with spontaneous chemiluminescence, or the carbonyl groups that are formed can be formed as part of a fluorescent group or be capable of undergoing subsequent reactions that lead to a fluorescent molecule. Alternatively, this dissociation reaction can lead to separation of a quenching group from a fundamentally fluorescent group that thereby regains its fluorescent property.

Another type of reaction of singlet oxygen with olefins is 4×2 cycloaddition with dienes, usually aromatic compounds such as naphthalenes, anthracenes, oxazoles, furans, indoles, and the like. Such a reaction leads initially to an endoperoxide. In some cases endoperoxides can rearrange to active esters or anhydrides that are capable of reaction with a suitably placed group to provide a lactone or lactam that can be fluorescent. Alternatively, the endoperoxides may oxidize a fluorescent or chemiluminescent compound precursor. Endoperoxides can also dissociate spontaneously or on heating with chemiluminescent emission or oxidize a fluorescent leuco dye.

Still another type of reaction of singlet oxygen with olefins is the "ene" reaction that produces an allylhydroperoxide. Suitable olefins have a reactive saturated C—H attached to an olefinic carbon. This product can react with an active ester in the same molecule to form a dioxetanone that can spontaneously or by heating dissociate with chemiluminescent emission.

In general, olefins of interest are those that undergo a chemical reaction upon reaction with singlet oxygen to form a metastable reaction product, usually a dioxetane or endoperoxide, which is capable of decomposition with the simultaneous or subsequent emission of light, usually within the wavelength range of 250 to 1200 nm. Preferred are electron rich olefins usually containing electron-donating groups. Exemplary of such electron rich olefins are enol ethers, enamines, 9-alkylidene-N-alkylacridans, arylvinylethers, 1,4-dioxenes, 1,4-thioxenes, 1,4-oxazines, arylimidazoles, 9-alkylidene-xanthanes and lucigenin.

The luminescence produced upon reaction of the olefins of interest with singlet oxygen will preferably be at wavelengths above 300 nanometers, preferably above 500 nanometers, and more preferably above 550 nm. Compounds that absorb light at wavelengths beyond the region where the sample components contribute significantly to light absorption will be of particular use in the present invention. The absorbance of serum drops off rapidly above 500 nm and becomes insignificant above 600 nm. Luminescence above 550 nm is of particular interest. However, luminescence at shorter wavelengths is useful when interference absorbance of the sample is absent. Preferably, the chemiluminescent olefins will absorb light at less than about 400 nm to permit convenient handling in room light without the risk of inadvertently producing singlet oxygen by photosensitization.

Examples of suitable electron rich chemiluminescent olefins are set forth in U.S. patent application Ser. No. 07/923,069, now abandoned, at page 64, line 8, to page 76, line 11, the disclosure of which is incorporated herein by reference. Such olefins generally have an electron-donating group in conjugation with the olefin.

The dioxetanes may be luminescent alone or in conjunction with a fluorescent energy acceptor. Enol ethers are examples of such olefins. Frequently, the enol ether compounds will have at least one aryl group bound to the olefinic carbons where the aryl ring is substituted with an electron donating group at a position that increases the reactivity of the olefin to singlet oxygen and/or imparts fluorescence to the product of dissociation of the resultant dioxetane. The electron-donating group can be, for example, hydroxyl, alkoxy, disubstituted amino, alkyl thio, furyl, pyryl, etc. Preferably, the enol ethers have an electron-donating group bound directly to an olefinic carbon.

Enamines are another example of such olefins. In general, useful enamines will be governed by the rules set forth above for enol ethers.

Another family of chemiluminescers is the 2,4,5-triphenylimidazoles, with lophine as the common name for the parent product. Chemiluminescent analogs include para-dimethylamino and -methoxy substituents.

Other chemiluminescent olefins that satisfy the requirements given above may be found in European Patent Application No. 0,345,776.

Fluorescent energy acceptor—as mentioned above, at least one of the chemiluminescent compositions has a fluorescent energy acceptor in close proximity to the chemiluminescer. Typically, the fluorescent energy acceptor is a chromophore having substantial absorption higher than 310 nm, normally higher than 350 nm, and preferably higher than about 400 nm. The width of the emission band at half peak height will usually be less than 100 nm, preferably less than 50 nm, more preferably, less than 25 nm. The choice of the fluorescent energy acceptor will be governed primarily by the particular chemiluminescer and the desired wavelength and lifetime of emission. The fluorescent energy acceptor should be capable of absorbing light emitted by the chemiluminescer. Preferably, the absorption maximum of the fluorescent energy acceptor should be at similar wavelength as the emission maximum of the chemiluminescer. A high extinction coefficient is desirable, usually in excess of 10, preferably in excess of $10^3$, and particularly preferred in excess of $10^4$. The fluorescent energy acceptor preferably has a high fluorescence quantum yield, usually at least 0.1, preferably greater than 0.4.

Preferred fluorescent energy acceptors are long wavelength, preferably hydrophobic, emitters including polycyclic aromatic hydrocarbons such as anthracenes, e.g., bisphenylethynylanthracene; coumarins; naphthacenes; phthalocyanines; squaraines, bis-(4-dimethlyaminophenyl) squaraine; porphyrins; polyacetylenes, oxazine dyes; rare earth chelates, especially, Eu, Tb and Sm, and the like. In general these dyes act as acceptors in energy transfer processes and preferably have high fluorescent quantum yields and do not react rapidly with singlet oxygen. They can be incorporated into matrices together with the chemiluminescer. Hydrophilic fluorescent dyes may also be used, particularly cyanine dyes, xanthenes such as fluorescein and Texas red, and umbelliferones.

A number of different molecules useful as the fluorescent energy acceptor are described by Ullman, et a. in U.S. Pat. Nos. 4,261,968, 4,174,384, 4,199,559 and 3,996,345, at columns 8 and 9, the relevant portions of which are incorporated herein by reference.

The label reagent or chemiluminescent composition of the present invention is generally associated with a matrix such as a particle. The chemiluminescer and fluorescent energy acceptor, when one is employed, are associated with a matrix as described above. As used herein, the term "associated with" includes the following: The association may be through covalent or non-covalent binding or through incorporation into the matrix.

The fluorescent energy acceptor may be formed as a result of a compound that reacts with singlet oxygen to form a fluorescent compound or a compound that can react with an auxiliary compound that is thereupon converted to a fluorescent compound. The fluorescent energy acceptor may be incorporated as part of a compound that also includes the chemiluminescer. For example, the fluorescent energy acceptor may include a metal chelate of a rare earth metal such as, e.g., europium, samarium, tellurium and the like. These materials are particularly attractive because of their sharp band of luminescence.

Sensitizer—a molecule, usually a compound, for generation of singlet oxygen. Preferably, the sensitizer is a photosensitizer. However, other sensitizers include, by way of example and not limitation, other substances and compositions that can produce singlet oxygen with or, less preferably, without activation by an external light source. Thus, for example, molybdate ($MoO_4^-$) salts and chloroperoxidase and myeloperoxidase plus bromide or chloride ion (Kanofsky, J. Biol. Chem. (1983) 259:5596) have been shown to catalyze the conversion of hydrogen peroxide to singlet oxygen and water. Either of these compositions can, for example, be included in particles to which is bound an sbp member and used in the assay method wherein hydrogen peroxide is included as an ancillary reagent, chloroperoxidase is bound to a surface and molybdate is incorporated in the aqueous phase of a liposome. Also included within the scope of the invention as photosensitizers are compounds that are not true sensitizers but which on excitation by heat, light, ionizing radiation, or chemical activation will release a molecule of singlet oxygen. The best known members of this class of compounds includes the endoperoxides such as 1,4-biscarboxyethyl-1,4-naphthalene endoperoxide, 9,10-diphenylanthraced-9,10-endoperoxide and 5,6,11,12-tetraphenyl naphthalene 5,12-endoperoxide. Heating or direct absorption of light by these compounds releases singlet oxygen.

Photosensitizer—a sensitizer for generation of singlet oxygen usually by excitation with light. The photosensitizer can be photoactivatable (e.g., dyes and aromatic compounds) or chemi-activated (e.g., enzymes and metal salts). When excited by light the photosensitizer is usually a compound comprised of covalently bonded atoms, usually with multiple conjugated double or triple bonds. The compound should absorb light in the wavelength range of 200–1100 nm, usually, 300–1000 nm, preferably, 450–950 nm, with an extinction coefficient at its absorbance maximum greater than 500 $M^{-1}$ $cm^{-1}$, preferably, 5000 $M^{-1}$ $cm^{-1}$, more preferably, 50000 $M^{-1}$ $cm^{-1}$, at the excitation wavelength. The lifetime of an excited state produced following absorption of light in the absence of oxygen will usually be at least 100 nanoseconds, preferably, at least 1 millisecond. In general, the lifetime must be sufficiently long to permit energy transfer to oxygen, which will normally be present at concentrations in the range of $10^{-5}$ to $10^{-3}$ M depending in the medium. The photosensitizer excited state will usually have a different spin quantum number (S) than its ground state and will usually be a triplet (S=1) which, as is usually the case, the ground state is a singlet (S=0). Preferably, the photosensitizer will have a high intersystem crossing yield. That is, photoexcitation of a photosensitizer will produce the long-lived state (usually triplet) with an efficiency of at least 10%, desirably at least 40%, preferably greater than 80%.

Photosensitizers that are to be excited by light will be relatively photostable and, preferably, will not react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3–6 of the periodic table, especially iodine or bromine, or they may have extended aromatic structures. Typical photosensitizers include acetone, benzophenone, 9-thioxanthone, eosin, 9,10-dibromoanthracene, methylene blue, metalloporphyrins, such as hematoporphyrin, phthalocyanines, chlorophylls, rose bengal, buckminsterfullerene, etc., and derivatives of these compounds having substituents of 1 to 50 atoms for rendering such compounds more lipophilic or more hydrophilic and/or as attaching groups for attachment, for example, to an sbp member. Examples of other photosensitizers that may be utilized in the present invention are those that have the above properties and are enumerated in N. F. Turro, "Molecular Photochemistry" page 132, W. A. Benjamin Inc., N.Y. 1965.

The photosensitizers are preferably relatively non-polar to assure dissolution into a lipophilic member when the photosensitizer is incorporated in an oil droplet, liposome, latex particle, etc.

Matrix—a support comprised of an organic or inorganic, solid or fluid, water insoluble material, which may be transparent or partially transparent. The primary requirement of the matrix is that it permit the diffusion of singlet oxygen therein at least to the proximate location of the incorporated label reagent. The matrix can have any of a number of shapes, such as particle, including bead, film, membrane, tube, well, strip, rod, and the like. The surface of the matrix is, preferably, hydrophilic or capable of being rendered hydrophilic. The body of the matrix is, preferably, hydrophobic. The matrix may be suspendable in the medium in which it is employed. Examples of suspendable matrices in accordance with the present invention, by way of illustration and not limitation, are polymeric materials such as latex, lipid bilayers, oil droplets, cells and hydrogels. Other matrix compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials.

Binding of sbp members to the matrix may be direct or indirect, covalent or non-covalent and can be accomplished by well-known techniques, commonly available in the literature. See, for example, "Immobilized Enzymes," Ichiro Chibata, Halsted Press, New York (1978) and Cuatrecasas, J. Biol. Chem., 245:3059 (1970).

The surface of the matrix will usually be polyfunctional or be capable of being polyfunctionalized or be capable of binding to an sbp member, or the like, through covalent or specific or non-specific non-covalent interactions. Such binding is indirect where non-covalent interactions are used and is direct where covalent interactions are employed. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well known and is amply illustrated in the literature (see above). The length of a linking group to the oligonucleotide or sbp member may vary widely, depending upon the nature of the compound being linked, the effect of the distance between the compound being linked and the surface on the specific binding properties and the like.

The chemiluminescent composition may be incorporated into the matrix either during or after the preparation of the matrix. The chemiluminescent composition is usually chosen to dissolve in the matrix but may be covalently attached to the matrix. The chemiluminescent compositions, when not covalently attached, are usually hydrophobic to reduce their ability to dissociate from the matrix. In general the matrix composition is chosen so as to favor association of the label reagent with the matrix.

The amount of chemiluminescent composition associated with or incorporated into the matrix in the compositions of the invention depends upon a number of factors such as the nature of the chemiluminescent composition and the matrix and the intended use of the resulting reagent. The chemiluminescent composition is present in the matrix in an amount necessary to maximize the signal produced in accordance with the invention, i.e., to provide the highest signal to background in an assay. Generally, the amount of chemiluminescent composition is determined empirically and is usually about from $10^{-8}$ to 1M, preferably, from $10^{-5}$ to $10^{-1}$ M, more preferably, $10^{-3}$ to $10^{-1}$ M.

In general, the sbp member will be present in from about 0.5 to 100, more usually 1 to 90, frequently from about 5 to 80 and preferably from about 50 to 100 mole percent of the molecules present on the surface of the matrix. The particular amount of sbp member is also dependent on a number of factors and is usually best determined empirically.

Particles—particles of at least about 20 nm and not more than about 20 microns, usually at least about 40 nm and less than about 10 microns, preferably from about 0.10 to 2.0 microns diameter, normally having a volume of less than 1 picoliter. The particle may have any density, but preferably of a density approximating water, generally from about 0.7 to about 1.5 g/ml. The particles may or may not have a charge, and when they are charged, they are preferably negative. The particles may be solid (e.g., comprised of organic and inorganic polymers or latex), oil droplets (e.g., hydrocarbon, fluorocarbon, silicon fluid), or vesicles (e.g., synthetic such as phospholipid or natural such as cells land organelles).

The solid particles are normally polymers, either addition or condensation polymers, which are readily dispersible in the assay medium. The solid particles will also be adsorptive or functionalizable so as to bind or attach at their surface, either directly or indirectly, an sbp member and to incorporate within their volume a label capable of being modified by singlet oxygen such as a chemiluminescent olefin.

The solid particles can be comprised of polystyrene, polyacrylamide, homopolymers and copolymers of derivatives of acrylate and methacrylate, particularly esters and amides, silicones and the like.

The particles may be bound or attached to an sbp member as described above.

Oil droplets—are water-immiscible fluid particles comprised of a lipophilic compound coated and stabilized with an emulsifier that is an amphiphilic molecule such as, for example, phospholipids, sphingomyelin, albumin and the like that exist as a suspension in an aqueous solution, i.e. an emulsion.

The phospholipids are based upon aliphatic carboxylic acid esters of aliphatic polyols, where at least one hydroxylic group is substituted with a carboxylic acid ester of from about 8 to 36, more usually of from about 10 to 20 carbon atoms, which may have from 0 to 3, more usually from 0 to 1 site of ethylenic unsaturation and at least 1, normally only 1, hydroxyl group substituted with phosphate to form a phosphate ester. The phosphate group may be further substituted with small aliphatic compounds that are difunctional or of higher functionality, generally having hydroxyl or amino groups.

Emulsions comprising oil droplets can be made in accordance with conventional procedures by combining the appropriate lipophilic compounds with a surfactant, anionic, cationic or nonionic, where the surfactant is present in from about 0.1 to 5, more usually from about 0.1 to 2 weight percent of the mixture and subjecting the mixture in an aqueous medium to agitation, such as sonication or vortexing. Illustrative lipophilic compounds include hydrocarbon oils, halocarbons including fluorocarbons, alkyl phthalates, trialkyl phosphates, triglycerides, etc. The following is a list, by way of illustration and not limitation, of amphiphilic compounds, which may be utilized for stabilizing oil droplets: phosphatidyl ethanolamine, phosphatidyl choline, phosphatidyl serine, dimyristoylphosphatidyl choline, egg phosphatidyl choline, dipalmitoylphosphatidyl choline, phosphatidic acid, cardiolipin, lecithin, galactocerebroside, sphingomyelin, dicetylphosphate, phosphatidyl inositol, 2-trihexadecylammoniumethylamine, 1,3-bis(octadecyl phosphate)-propanol, stearoyloxyethylene phosphate, phospholipids, dialkylphosphates, sodium dodecyl sulfate, cationic detergents, anionic detergents, proteins such as albumin, non-ionic detergents, etc.

Other compounds may also be used which have lipophilic groups and which have been described previously. For the most part, these compounds have a lipophilic component such as an alkylbenzene, having alkyl groups of from 6 to 20 carbon atoms, usually mixtures of alkyl groups, which may be straight or branched chain, and a hydrophilic component such as a carboxyl group, an hydroxylic group, a polyoxy alkylene group (alkylene of from 2 to 3 carbon atoms), sulfonic acid group, or amino group. Aliphatic fatty acids may be used which will normally be of from about 10 to 36, more usually of from about 12 to 20 carbon atoms. Also, fatty alcohols having the carbon limits indicated for the fatty acids, fatty amines of similar carbon limitations and various steroids may also find use.

The oil droplets can comprise a fluorocarbon oil or a silicone oil (silicon particle). Such droplets are described by Giaever in U.S. Pat. Nos. 4,634,681 and 4,619,904 (the disclosures of which are incorporated herein in their entirety). These droplets are formed by dispersing a fluorocarbon oil or silicone oil in an aqueous phase. The droplets are prepared by placing a small amount of the selected oil (generally, such oils are commercially available) in a container with a larger amount of the aqueous phase. The liquid system is subjected to agitation to bring about emulsification and then centrifuged. The homogeneous phase is removed and the residual droplets are resuspended in an aqueous buffered medium. The above centrifugation and decantation steps can be repeated one or more times before the droplets are utilized.

Sbp members, and where appropriate the label reagent, can be bound to the droplets in a number of ways. As described by Giaever, supra, the particular sbp member, e.g., a proteinaceous sbp member, can be coated on the droplets by introducing an excess of the sbp member into the aqueous medium prior to or after the emulsification step. Washing steps are desirable to remove excess sbp member. Functionalization of the oil introduces functionalities described above for linking to sbp members.

A chemiluminescent olefin as a label is often chosen to be soluble in the oil phase of the oil droplet. When the oil is a fluorocarbon, a fluorinated chemiluminescent olefin is often more soluble than the corresponding unfluorinated derivation.

Other oil droplets described by Giaever also find use in the present invention.

Liposomes—microvesicles comprised of one or more lipid bilayers having approximately spherical shape and one of the preferred materials for use in the present invention. The liposomes have a diameter that is at least about 20 nm and not more than about 20 microns, usually at least about 40 nm and less than about 10 microns. Preferably, the diameter of the liposomes will be less than about two microns so as to limit settling or floatation.

The outer shell of a liposome consists of an amphiphilic bilayer that encloses a volume of water or an aqueous solution. Liposomes with more than one bilayer are referred to as multilamellar vesicles. Liposomes with only one bilayer are called unilamellar vesicles. Multilamellar vesicles are preferred in the present invention when using a lipophilic chemiluminescent olefin because of their ability to incorporate larger quantities of this material than with unilamellar vesicles. The amphiphilic bilayer is frequently comprised of phospholipids. Phospholipids employed in preparing particles utilizable in the present invention can be any phospholipid or phospholipid mixture found in natural membranes including lecithin, or synthetic glyceryl phosphate diesters of saturated or unsaturated 12-carbon or 24-carbon linear fatty acids wherein the phosphate can be present as a monoester, or as an ester of a polar alcohol such as ethanolamine, choline, inositol, serine, glycerol and the like. Particularly preferred phospholipids include L-a-palmitoyl oleoyl-phosphatidylcholine (POPC), palmitoyl oleoylphosphatidyl-glycerol (POPG), L-α-dioleoylphosphatidylglycerol, L-α (dioleoyl)-phosphatidyl ethanolamine (DOPE) and L-α-(dioleoyl)-phosphatidyl-(4-(N-maleimidomethyl)-cyclohexane-1-carboxyamido) ethanol (DOPE-MCC).

The phospholipids in the bilayer may be supplemented with cholesterol and may be replaced with other amphiphilic compounds that have a polar head group, usually charged, and a hydrophobic portion usually comprised of two linear hydrocarbon chains. Examples of such substituents include dialkylphosphate, dialkoxypropylphosphates wherein the alkyl groups have linear chains of 12–20 carbon atoms, N-(2,3-di-(9-(Z)-octa-decenyloxy))-prop-1-yl-N,N,N-trimethyl-ammonium chloride (DOTMA), as disclosed in U.S. patent application Ser. No. 811,146 filed on December 19, 1985, which is hereby incorporated herein by reference, sphingomyelin, cardiolipin, and the like.

Liposomes utilized in the present invention preferably have a high negative charge density to stabilize the suspension and to prevent spontaneous aggregation.

For use in the present invention the liposomes should be capable of binding to an sbp member and be capable of having a chemiluminescent composition associated with either the aqueous or the nonaqueous phase.

Liposomes may be produced by a variety of methods including hydration and mechanical dispersion of dried phospholipid or phospholipid substitute in an aqueous solution. Liposomes prepared in this manner have a variety of dimensions, compositions and behaviors. One method of reducing the heterogeneity and inconsistency of behavior of mechanically dispersed liposomes is by sonication. Such a method decreases the average liposome size. Alternatively, extrusion is usable as a final step during the production of the liposomes. U.S. Pat. No. 4,529,561 discloses a method of extruding liposomes under pressure through a uniform pore-size membrane to improve size uniformity.

Preparation of liposomes containing a chemiluminescent olefin dissolved in the lipid bilayer can be carried out in a variety of methods, including a method described by Olsen, et al., *Biochemica et Biophysica Acta*, 557(9), 1979. Briefly, a mixture of lipids containing the appropriate chemiluminescent olefin in an organic solvent such as chloroform is dried to a thin film on the walls of a glass vessel. The lipid film is hydrated in an appropriate buffer by shaking or vortexing. Thereafter, the lipid suspension is extruded through a series of polycarbonate filter membranes having successively smaller pore sizes, for example, 2.0, 1.0, 0.8, 0.6, 0.4, and 0.2 microns. Repeated filtration through any of the filters, and in particular through the smallest filter, is desirable. The liposomes can be purified by, for example, gel filtration, such as through a column of Sephacryl S-1000. The column can be eluted with buffer and the liposomes collected. Storage in the cold prolongs shelf life of the liposomes produced by this method. Alternatively, the chemiluminescent olefin can be added to the liquid suspension following preparation of the liposomes.

Liposomes and oil droplets will often have, for example, thiol or maleimide or biotin groups on the molecules comprising the lipid bilayer. Sbp members may then be bound to the surface by reaction of the particles with one of these materials that is bound to a sulfhydryl reactive reagent, a sulfhydryl group, or avidin, respectively. Sulfhydryl reactive groups include, among others, activated disulfides such as 2-pyridyl disulfides and alkylating reagents such as bromoacetamide and maleimide.

Sbp members and members of the label reagent can be attracted to the surface of the liposome particles by weak hydrophobic interactions, however such interactions are not generally sufficient to withstand the shear force encountered during incubation and washing. It is preferable to covalently bond such molecules and sbp members to a liposome particle that has been functionalized, for example by use of DOPE-MCC, as shown above, by combining the liposome with the selected molecule or sbp member functionalized with a mercaptan group. For example, if the sbp member is an antibody, it may be reacted with S-acetyl-mercaptosuccinic anhydride (SAMSA) and hydrolyzed to provide a sulfhydryl-modified antibody. Other examples include the N-hydroxysuccinimide ester of surface carboxyl groups, which are then contacted with a linker having amino groups that will react with the ester groups or directly with an sbp member that has an amino group. The linker will usually be selected to reduce nonspecific binding of assay components to the particle surface and will preferably provide suitable functionality for both attachment to the particle and attachment of the sbp member. Suitable materials include maleimidated aminodextran (MAD), polylysine, aminosaccharides, and the like. MAD can be prepared as described by Hubert, et al., *Proc. Natl. Acad. Sci.*, 75(7), 3143, 1978.

Latex particles—"Latex" signifies a particulate water suspendable water insoluble polymeric material usually having particle dimensions of 20 nm to 20 mm, more preferably 100 to 1000 nm in diameter. The latex is frequently a substituted polyethylene such as polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyridine, vinyl-chloride acrylate copolymers, and the like. Non-crosslinked polymers of styrene and carboxylated styrene or styrene functionalized with other active groups such as amino, hydroxyl, halo and the like are preferred. Frequently, copolymers of substituted styrenes with dienes such as butadiene will be used.

The association of the label reagent with latex particles utilized in the present invention may involve incorporation during formation of the particles by polymerization but will usually involve incorporation into preformed particles, usually by noncovalent dissolution into the particles. Usually, a solution of the label will be employed particularly where the label is a chemiluminescent olefin. Solvents that may be utilized include alcohols, including ethanol, ethylene glycol and benzyl alcohol; amides such as dimethyl formamide, formamide, acetamide and tetramethyl urea and the like; sulfoxides such as dimethyl sulfoxide and sulfolane; and ethers such as carbitol, ethyl carbitol, dimethoxy ethane and the like, and water. The use of solvents having high boiling points in which the particles are insoluble permits the use of elevated temperatures to facilitate dissolution of the label compounds into the particles and are particularly suitable. The solvents may be used singly or in combination.

For incorporating chemiluminescers in particles, solvents should be selected that do not interfere with the luminescence because of their intrinsic properties or because they can be removed from the particles. Frequently, hydroxylic solvents are also preferred. Typical aromatic cosolvents including dibutylphthalate, benzonitrile, naphthonitrile, dioctylterephthalate, dichlorobenzene, diphenylether, dimethoxybenzene, etc, will be used at sufficiently low concentrations to avoid dissolution of the particles but at sufficient concentrations to swell the particles.

Generally, the temperature employed during the procedure will be chosen to maximize the singlet oxygen formation and the quantum yield of the chemiluminescer associated with the particles with the proviso that the particles should not melt or become aggregated at the selected temperature. Elevated temperatures are normally employed. The temperatures for the procedure will generally range from 20° C. to 200° C., more usually from 50° C. to 170° C. It has been observed that some compounds that are nearly insoluble at room temperature, are soluble in, for example, low molecular weight alcohols, such as ethanol and ethylene glycol and the like, at elevated temperatures. Carboxylated modified latex particles have been shown to tolerate low molecular weight alcohols at such temperatures.

An sbp member or member of the label reagent may be physically adsorbed on the surface of the latex particle or may be covalently bonded or attached to the particle in a manner similar to that discussed above with respect to other matrices.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Polynucleotide—a compound or composition which is a polymeric nucleotide having in the natural state about 50 to 500,000 or more nucleotides and having in the isolated state about 15 to 50,000 or more nucleotides, usually about 15 to 20,000 nucleotides, more frequently 15 to 10,000 nucleotides. The polynucleotide includes nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

Ligand—any organic compound for which a receptor naturally exists or can be prepared.

Ligand analog—a modified ligand, an organic radical or analyte analog, usually of a molecular weight greater than 100, which can compete with the analogous ligand for a receptor, the modification providing means to join a ligand analog to another molecule. The ligand analog will usually differ from the ligand by more than replacement of a hydrogen with a bond that links the ligand analog to a hub or label, but need not. The ligand analog can bind to the receptor in a manner similar to the ligand. The analog could be, for example, an antibody directed against the idiotype of an antibody to the ligand.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, and the like.

Specific binding—the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme—substrate interactions, polynucleotide interactions, and so forth.

Non-specific binding—non-covalent binding between molecules that is relatively independent of specific surface structures. Non-specific binding may result from several factors including hydrophobic interactions between molecules.

Antibody—an immunoglobulin that specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7:1–24 (1975); Broughton and Strong, Clin. Chem. 22: 726–732 (1976); and Playfair, et al., Br. Med. Bull. 30: 24–31 (1974).

Antibodies can also be obtained by somatic cell hybridization techniques, such antibodies being commonly referred to as monoclonal antibodies. Monoclonal antibodies may be produced according to the standard techniques of Köhler and Milstein, Nature 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 346 (1981). Samples of an appropriate immunogen preparation are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

In another approach for the preparation of antibodies the sequence coding for antibody binding sites can be excised from the chromosome DNA and inserted into a cloning vector which can be expressed in bacteria to produce recombinant proteins having the corresponding antibody binding sites.

In general, antibodies can be purified by known techniques such as chromatography, e.g., DEAE chromatography, ABx chromatography, and the like, filtration, and so forth.

Substituted—means that a hydrogen atom of a molecule has been replaced by another atom, which may be a single atom such as a halogen, etc., or part of a group of atoms forming a functionality such as a substituent having from 1 to 50 atoms (other than the requisite hydrogen atoms necessary to satisfy the valencies of such atoms), which atoms are independently selected from the group consisting of carbon, oxygen, nitrogen, sulfur, halogen (chlorine, bromine, iodine, fluorine) and phosphorus, and which may or may not be bound to one or more metal atoms.

Electron-donating group—a substituent which, when bound to a molecule, is capable of polarizing the molecule such that the electron-donating group becomes electron poor and positively charged relative to another portion of the molecule, i.e., has reduced electron density. Such groups include, by way of illustration and not limitation, amines, ethers, thioethers, phosphines, hydroxy, oxyanions, mercaptans and their anions, sulfides, etc.

A substituent having from 1 to 50 atoms (other than the requisite hydrogen atoms necessary to satisfy the valencies of such atoms), which atoms are independently selected from the group consisting of carbon, oxygen, nitrogen, sulfur, halogen and phosphorus—an organic radical; the organic radical has 1 to 50 atoms other than the requisite number of hydrogen atoms necessary to satisfy the valencies of the atoms in the radical. Generally, the predominant atom is carbon (C) but may also be oxygen (O), nitrogen (N), sulfur (S), phosphorus (P), wherein the O, N, S, or P, if present, are bound to carbon or one or more of each other or to hydrogen or a metal atom to form various functional groups, such as, for example, carboxyl groups (carboxylic acids), hydroxyl groups (alcohols), mercapto groups (thiols), carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes and nitriles, and alkyl, alkylidine, aryl, aralkyl, and alkyl, aryl, and aralkyl substituted with one or more of the aforementioned functional groups, e.g., phenyl, naphthyl, phenanthryl, m-methoxyphenyl, dimethylamino, trityl, methoxy, N-morpholino and may be taken together to form a ring such as, for example, adamantyl, N-methyacridanylide, xanthanylidine, 1-(3,4-benzo-5-hydrofurylidene), and the like.

Linking group—a group involved in the covalent linkage between molecules. The linking group will vary depending upon the nature of the molecules, i.e., label, matrix, sbp member or molecule associated with, or part of, a particle being linked. Functional groups that are normally present or are introduced on a matrix or an sbp member will be employed for linking these materials.

For the most part, carbonyl functionalities will find use, both oxocarbonyl, e.g., aldehyde, and non-oxocarbonyl (including nitrogen and sulfur analogs) e.g., carboxy, amidine, amidate, thiocarboxy and thionocarboxy.

Alternative functionalities of oxo include active halogen, diazo, mercapto, olefin, particularly activated olefin, amino, phosphoro and the like. A description of linking groups may be found in U.S. Pat. No. 3,817,837, which disclosure is incorporated herein by reference in its entirety.

The linking groups may vary from a bond to a chain of from 1 to 100 atoms, usually from about 1 to 70 atoms, preferably I to 50 atoms more preferably 1 to 20 atoms, each independently selected from the group normally consisting of carbon, oxygen, sulfur, nitrogen, halogen and phosphorous. The number of heteroatoms in the linking groups will normally range from about 0 to 20, usually from about 1 to 15, more preferably 2 to 6. The atoms in the chain may be substituted with atoms other than hydrogen in a manner similar to that described above for the substituent having from 1 to 50 atoms. As a general rule, the length of a particular linking group can be selected arbitrarily to provide for convenience of synthesis and the incorporation of any desired group such as an energy acceptor, fluorophor, group for analysis of intersystem crossing such as a heavy atom, and the like. The linking groups may be aliphatic or aromatic, although with diazo groups, aromatic groups will usually be involved.

When heteroatoms are present, oxygen will normally be present as oxo or oxy, bonded to carbon, sulfur, nitrogen or phosphorous, nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester.

Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

For the most part, when a linking group will have a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or $\alpha$-, $\beta$-unsaturated ester. These functionalities will be linked to amine groups, carboxyl groups, active olefins, alkylating agents, e.g., bromoacetyl. Where an amine and carboxylic acid or its nitrogen derivative or phosphoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed.

A group or functionality imparting hydrophilicity or water solubility—is a hydrophilic functionality, which increases wettability of solids with water and the solubility in water of compounds to which it is bound. Such functional group or functionality can be a substituent having 1 to 50 or more atoms and can include a group having a sulfonate, sulfate, phosphate, amidine, phosphonate, carboxylate, hydroxyl particularly polyols, amine, ether, amide, and the like. Illustrative functional groups are carboxyalkyl, sulfonoxyalkyl, $CONHOCH_2COOH$, $CO$-(glucosamine), sugars, dextran, cyclodextrin, $SO_2NHCH_2COOH$, $SO_3H$, $CONHCH_2CH_2SO_3H$, $PO_3H_2$, $OPO_3H_2$, hydroxyl, carboxyl, ketone, and combinations thereof. Most of the above functionalities can also be utilized as attaching groups, which permit attachment of an sbp member or the like to a particulate composition comprised of the label.

A group or functionality imparting lipophilicity or lipid solubility—is a lipophilic functionality, which decreases the wettability of surfaces by water and the solubility in water of compounds to which it is bound. Such functional group or functionality can contain 1 to 50 or more atoms, usually carbon atoms substituted with hydrogen or halogen and can include alkyl, alkylidene, aryl and aralkyl. The lipophilic group or functionality will normally have one to six straight or branched chain aliphatic groups of at least 6 carbon atoms, more usually at least 10 carbon atoms, and preferably at least 12 carbon atoms, usually not more than 30 carbon atoms. The aliphatic group may be bonded to rings of from 5 to 6 members, which may be alicyclic, heterocyclic, or aromatic. Lipophilic groups may be bonded to a label or other substance to increase its solubility in a non-aqueous matrix.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

As mentioned above, the present method is directed to the determination of the presence or relative amounts of two or more components in a medium. A combination is provided comprising a medium suspected of containing the components and a label reagent for each of the components. The label reagent comprises a first specific binding pair (sbp) member associated with a chemiluminescent composition. Luminescence emitted by each of the chemiluminescent compositions upon activation is differentially detectable. The first sbp member is capable of binding to the component or to a second sbp member to form a complex related to the amount of the component. At least one of the chemiluminescent compositions comprises a fluorescent energy acceptor. After the above are combined, the chemiluminescent compositions are activated. The amount of luminescence generated by each of the chemiluminescent compositions is detected and related to the amount of each of the components in the medium.

As mentioned above, the label reagent usually comprises a matrix, preferably in the form of particles, with which the chemiluminescer and fluorescent energy acceptor are associated. The matrix has the chemiluminescer and/or the fluorescent energy acceptor incorporated therein and/or bound to its surface. The amount of the chemiluminescer in the chemiluminescent composition is usually about up to about 20% of the weight of the matrix, usually about 1–20%, preferably at least about 0.01%, usually at least about 0.1%. The amount of the fluorescent energy acceptor in the chemiluminescent composition is usually about $10^{-7}$ to about $10^{-1}$ M, preferably about $10^{-5}$ to about $10^{-2}$ M.

It is also in the purview of the present invention to have more than one energy acceptors in the chemiluminescent composition. In this regard additional energy acceptors are employed to optimize the transfer of energy from the chemiluminescers to the fluorescent energy acceptors. Energy acceptors that provide this function preferably absorb light efficiently at the wavelength of emission of the chemiluminescer. When they are fluorescent they will preferably emit at a wavelength close to the absorption maximum of the fluorescent energy acceptor. For example 9,10-bis-phenylethynylantracene serves to increase the efficiency of energy transfer from thioxenes to rubrene upon activation of the thioxene with singlet oxygen. The amount of the additional chemiluminescers are determined empirically and are usually about $10^{-5}$ to about $10^{-1}$ M, preferably about $10^{-4}$ to about $10^{-2}$ M.

The assay is usually carried out in an aqueous buffered medium at a moderate pH, generally that which provides optimum assay sensitivity. The aqueous medium may be solely water or may include from 0.01 to 80 or more volume percent of a cosolvent. The pH for the medium will usually be in the range of about 4 to 13, more usually in the range of about 5 to 10, and preferably in the range of about 6.5 to 9.5. The pH is generally selected to achieve optimum assay sensitivity and specificity. Among the factors that must be considered are the pH dependence of the rates of the reactions involved, the binding of binding members and the minimization of non-specific binding, and so forth.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred.

Moderate temperatures are normally employed for carrying out the assay and usually constant temperature, preferably, room temperature, during the period of the measurement. Incubation temperatures will normally range from about 5° to 99° C., usually from about 15° to 70° C., more usually 20 to 45° C. Temperatures during measurements will generally range from about 10° to 70° C., more usually from about 20° to 45° C., more usually 20° to 25° C.

In some instances the activated chemiluminescer may require heating up to 100° C. in order to decay to produce luminescence because the product of its reaction is relatively stable at ambient temperatures. Relatively stable dioxetanes can be formed, for example, by reaction of singlet oxygen with adamantylidenes (see, e.g., McCapra, supra) and relatively stable endoperoxides can be formed by reaction of singlet oxygen with 1,4-disubstituted naphthalenes and anthracenes (see, e.g., N.J. Turro, Modern Molecular Photochemistry (1978) Benjamin Cummings Publishing Co. page 594). In both circumstances above, the stable materials will undergo decay upon heating, usually, at a temperature of less than 200° C., preferably about 50 to 100° C. Such heating causes the rapid decomposition of the singlet oxygen/olefin adduct and, thus, the emission of light occurs over a short period of time. The use of this approach may be desirable when separate signals from different chemiluminescers are difficult to fully resolve by lifetime and wavelength.

The concentration of components to be detected will generally vary from about $10^{-5}$ to $10^{-17}$ M, more usually from about $10^{-6}$ to $10^{-14}$ M. Considerations, such as whether the assay is qualitative, semiquantitative or quantitative, the particular detection technique and the nature and concentration of the component of interest will normally determine the concentrations of the various reagents.

While the concentrations of the various reagents in the assay medium will generally be determined by the concentration range of interest of the components to be detected, the final concentration of each of the reagents will normally be determined empirically to optimize the sensitivity of the assay over the range. That is, a variation in concentration of the components to be detected that is of significance should provide an accurately measurable signal difference.

While the order of addition may be varied widely, there will be certain preferences depending on the nature of the assay. The simplest order of addition is to add all the materials simultaneously. Alternatively, the reagents can be combined wholly or partially sequentially. One or more incubation steps may be involved after the reagents are combined, generally ranging from about 30 seconds to 6 hours, more usually from about 2 minutes to 1 hour.

Although the fluorescent energy acceptor that is used may provide some control of the rate of decay of the label reagent, other factors such as the structure of the chemiluminescer will usually provide more effective control. Structural features that contribute to a delay in luminescence are discussed by Schaap, supra, and McCapra, supra, wherein the relevant portions of these references are incorporated herein by reference.

Another factor that allows for control of the time to luminescence is the composition of the matrix such as the particle. In general, when the matrix is composed of a non-polar material in which the chemiluminescer is dissolved, decay times are increased in relation to polar materials.

Another factor that may be used to control the rate of luminescence is temperature. In general, increasing the temperature will decrease the decay time.

The luminescence or light produced for each label reagent as a result of the above can be measured visually, photographically, actinometrically, spectrophotometrically or by any other convenient means to determine the amount thereof, which is related to the amount of each component in the medium. Usually, light emitted from the label reagent is measured while the chemiluminescent material is in contact with the assay medium, for example, by means of a luminometer or a photosensitive material.

One particular application of the methods and compositions of the invention is a method for determining the presence or relative amounts of a plurality of analytes, each of which is a member of a specific binding pair (sbp). A combination is provided comprising a medium suspected of containing a plurality of analytes, a label reagent for each of the analytes, and a photosensitizer. Each label reagent comprises a first sbp member bound to a particle in which a chemiluminescer and a fluorescent energy acceptor are incorporated. Each of the label reagents has a different luminescent emission wavelength and/or rate of decay. Each first sbp member is capable of binding to the analyte or to a second sbp member to form a complex related to the amount of the respective analyte. The combination is incubated in a medium under conditions sufficient to allow the sbp members to bind to the analytes or to respective second sbp members. The medium is irradiated with light. The amount of luminescent emission generated by each of the label reagents is detected at a time after irradiation and at a wavelength corresponding to the rate of decay and wavelength of the respective luminescent emission. The amount of each measured luminescent emission is then related to the amount of each analyte in the medium.

The method and compositions of the invention may be adapted to most assays involving sbp members such as ligand-receptor, e.g., antigen-antibody reactions, polynucleotide binding assays, and so forth. The assays are usually homogeneous or heterogeneous, preferably homogeneous, including competitive and sandwich. In a specific binding assay, the sample may be pretreated, if necessary, to remove unwanted materials.

As mentioned previously, the first sbp member above is capable of binding to the analyte or to a second sbp member capable of binding to the analyte. When the second sbp member is also capable of binding to the analyte, a sandwich assay protocol can result. The immunological reaction for a sandwich type assay usually involves an sbp member, e.g., an antibody, that is complementary to the analyte, a second sbp member, e.g., antibody, that is also complementary to the analyte and bound to the particulate matrix, and the sample of interest.

One of the sbp members alternatively can be analogous to the analyte, in which case a competitive assay protocol can result. The immunological reaction for a competitive protocol usually involves an sbp member that is complementary to the analyte and an sbp member that is analogous to, usually a derivative of, the analyte. One of these sbp members will be associated with the matrix.

In one type of assay, a sample suspected of containing an analyte, which is an sbp member and the other assay components are combined with a particulate matrix of the present invention. The medium is then examined for the presence of chemiluminescent emission, usually by measuring the amount of light emitted, which is related to the amount of analyte in the sample. This approach is a homogeneous assay where a separation step is not employed. Alternatively, a particulate or non-particulate matrix may be used, which, after combining the assay components, may be separated from the liquid phase, and either the solid phase or the liquid phase may then be examined for the presence of chemiluminescent emission.

Preferred compositions in accordance with the present invention are latex particles, liposomes or oil droplets having incorporated therein a chemiluminescer and a fluorescent energy acceptor.

A typical assay protocol is described next by way of example and not limitation. A chemiluminescent composition of the present invention is attached to a specific binding reagent (for example: antibody, oligonucleotide, receptor, etc.) that is complementary to the analyte. A sensitizer particle is attached to a second specific binding reagent that is complementary to the analyte. In a sandwich assay format the analyte brings both the sensitizer and chemiluminescer particles in close proximity. Activation of sensitizer particles with light results in the formation of singlet oxygen, which is channeled to the particle label reagent. Usually the reaction of two or more different chemiluminescent compositions is initiated simultaneously and the resulting light emitted by each chemiluminescent composition is detected and measured sequentially. The chemiluminescent compositions with fast chemiluminescent decay are measured first followed by the slower chemiluminescent decaying compositions. The emitted light may be measured at three or more different wavelengths.

An important feature of the present invention is the design and selection of sets of chemiluminescent compositions that are capable of emitting signals sufficiently distinct from each other to be separately detected and quantitated upon excitation of the sensitizer.

The present invention also has application to assays that are not based on specific binding. For these types of assays, the differentiation of the analyses usually depends only on the wavelength of the emission rather than on lifetime. This is because most of the methods will provide a relatively steady state emission and lifetime cannot be conveniently measured. Examples of such combined assays are for components such as glucose and galactose, which can be measured simultaneously in a mixture containing glucose oxidase-lactoperoxidase chemiluminescer particles and galactose oxidase-lactoperoxidase chemiluminescer particles. The lactoperoxidase converts the hydrogen peroxide produced from the analyses into singlet oxygen, which reacts with the particular assay particles upon which it is generated. Other components that can be oxidized by oxidases and can be similarly determined in mixtures include d-amino acids, xanthene, cholesterol, oxalate, glycerol-1-phosphate, uric acid, etc. Similarly, multi-component assays can be performed for components that are substrates for NAD-dependent enzymes such as lactate, ethanol, triglycerides, 3α-hydroxybile acids, glucose-6-phosphate, glucose-1-phosphate, uric acid, D-β-hydroxybutyrate, etc. In these assays the appropriate enzymes are attached to the particles along with NADH oxidase and lactoperoxidase. The NADH formed from the analyte reacts with the oxidase to produce hydrogen peroxide that reacts with the lactoperoxidase in the presence of bromide ion to produce singlet oxygen, which in turn reacts with each of the different particles with light emission. In some of these examples the component will normally be the product of an enzyme reaction in which the enzyme may be the actual component of clinical interest.

By judicious choice of label reagents with different lifetimes and different emission maxima, assays may be carried out with high sensitivity and large dynamic range. Thus, simultaneous detection and quantitation of a plurality of components in a sample can be conducted. As mentioned above, the label reagents used in the present invention are most effective when activatable by singlet oxygen. The signals can be deconvoluted by use of lifetime and wavelength measurements, preferably, by the simultaneous use of both methods. Thus, for example, referring to Table 1, compositions 2, 7, and 9 permit detection at 410, 490, and 560 nm, respectively, and they have decay rates in latex particles of 0.6, 0.6, and 30 seconds, respectively. Quantitative discrimination between 410 and 490 nm is possible, but separation of the emissions at 490 and 560 nm is incomplete. However, because the lifetime of emission from composition 9 is very much longer than from 2 and 7, it is possible to delay detection of the former for a time period sufficient to achieve practically complete decay of the shorter lived dioxetanes. Other combinations can also work. For example, composition 3 and composition 5 can be differentiated by wavelength alone and composition 11 or 12 can be used in combination with 3 or 5 either by simple use of wavelength or by relying on the slower emission rates of 11 and 12. Another useful combination includes compositions 10, 6 and 11 where there is a time delay before measuring the emission from 11.

The following list of label reagents are provided in Table 1 by way of illustration and not limitation, wherein Ph is phenyl, t-Bu is tertiary butyl, and R is H. The label reagent comprises a chemiluminescer contained in a latex particle. The particle is preferably comprised of polymeric latex but may be oil droplets, liposomes or other materials suitable for incorporation of a chemiluminescent as described above. Most of the chemiluminescent compositions have a high quantum yield of chemiluminescence, 2% to 7% (reference: Luminol) and all the chemiluminophores react rapidly with singlet oxygen ($>10^8$ $M^{-1}S^{-1}$).

TABLE 1

| CHEMILUMINESCENT COMPOSITIONS | HALFLIFE Seconds at 37° C. (in Latex particles) | EMISSION Maxima nm |
|---|---|---|
| 1. | 0.6 | 390 |
| 2. | 0.6 | 410<br>430<br>390 (w)* |
| 3. | 0.6 | 410<br>390 (w)* |

TABLE 1-continued

| CHEMILUMINESCENT COMPOSITIONS | HALFLIFE Seconds at 37° C. (in Latex particles) | EMISSION Maxima nm |
|---|---|---|
| 4. [structure: bis(tetradecyl)amino-phenyl dioxene/dithiene + julolidine-coumarin with CO₂t-Bu] | 0.6 | 480<br>390 (w)* |
| 5. [structure: bis(tetradecyl)amino-phenyl dioxene/dithiene + julolidine-coumarin with acetyl] | 0.6 | 500<br>390 (w)* |
| 6. [structure: bis(tetradecyl)amino-phenyl dioxene/dithiene + 9,10-bis(phenylethynyl)anthracene] | 0.6 | 490<br>510<br>390 (w)* |
| 7. [structure: phenyl dioxene/dithiene-phenyl-N(Me)-(CH₂)₃-C(O)NH-anthracene(bis-phenylethynyl)] | 0.5 | 500 |
| 8. [structure: dimethylamino-phenyl morpholine/oxazine with R substituents] | 30 | 550 |

TABLE 1-continued

| CHEMILUMINESCENT COMPOSITIONS | HALFLIFE Seconds at 37° C. (in Latex particles) | EMISSION Maxima nm |
|---|---|---|
| 9. [structure: morpholine-dioxene with dimethylaminophenyl and phenyl substituents, N-aryl with R groups + rubrene (5,6,11,12-tetraphenyltetracene)] | 30 | 560 |
| 10. [structure: 2-(4-dimethylaminophenyl)-3-phenyl-1,4-dioxene] | 180 | 370 |
| 11. [structure: dioxene-dimethylaminophenyl-phenyl with CH$_2$-NH-C(O)- linked phenanthroline Eu(III) complex with three thenoyltrifluoroacetonate ligands] | 15 | 594<br>613 |
| 12. [structure: dioxene-dimethylaminophenyl-phenyl with CH$_2$-NH-C(O)- linked phenanthroline Sm(III) complex with three thenoyltrifluoroacetonate ligands] | 15 | 570<br>600<br>648 |

TABLE 1-continued

| CHEMILUMINESCENT COMPOSITIONS | HALFLIFE Seconds at 37° C. (in Latex particles) | EMISSION Maxima nm |
|---|---|---|
| 13. 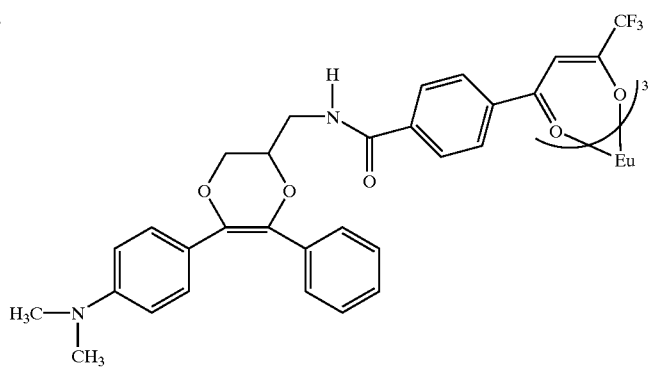 | 2.5 | 594<br>613 |

*weak thioxene emission is observed at 390 nm

The foregoing compositions and assays are provided by way of illustration and not limitation to enable one skilled in the art to appreciate the scope of the present invention and to practice the invention without undue experimentation. It will be appreciated that the choice of components, e.g., analytes, label reagents, particles, other reagents and reaction conditions will be suggested to those skilled in the art in view of the disclosure herein and the examples that follow.

Another aspect of the present invention relates to kits useful for conveniently performing an assay method of the invention for determining the presence or relative amounts of two or more components in a medium. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents.

A kit of the present invention comprises in packaged combination a plurality of label reagents and a sensitizer. Each label reagent comprises a chemiluminescent composition associated with a particle and a member of a specific binding pair (sbp). Each of the chemiluminescent compositions comprises an olefinic compound activatable by singlet oxygen and may also contain a fluorescent energy acceptor that controls the wavelength of the emission. Each of the chemiluminescent compositions has luminescent emissions of different wavelength and/or decay rate.

The sensitizer may be a photosensitizer such as a dye. The kit can further include other separately packaged reagents for conducting an assay such as enzyme substrates, additional sbp members, ancillary reagents and so forth.

The relative amounts of the various reagents in the kits can be varied widely to provide for concentrations of the reagents that substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

EXAMPLES

The invention is demonstrated further by the following illustrative examples. Parts and percentages recited herein are by weight unless otherwise specified. Temperatures are in degrees centigrade (° C.).

Melting points were determined on a Hoover capillary apparatus and are uncorrected. $^1$HNMR spectra were recorded on a Brucker WP-250 MHz or Brucker WP-300 MHz NMR spectrometer. Chemical shifts were reported in parts per million (δ0.0). NMR multiplicities are recorded by use of the following abbreviations: s, singlet; d, doublet; t, triplet; m, multiplet; Hz, hertz. Infrared spectra were recorded on a Perkin-Elmer 2971R spectrometer. Desorption chemical ionization (C.I.) and electron ionization (E.I.) were done on a Varian-MAT 311A, double focusing high-resolution mass spectrometer. A Finnigan TSQ-70 or MAT-8230 was used for fast atom bombardment mass spectra (FAB/LSIMS). UV-visible absorption spectra were done on a HP 8452A diode array spectrophotometer. Fluorescence and chemiluminescence measurements were done on a Spex fluorolog spectrophotometer or a Perkin Elmer 650-40 spectrophotometer. Chemiluminescence measurements were also performed on an in-house chemiluminometer (Oriel box).

Toluene was distilled from sodium over argon. Unless mentioned otherwise, all solvents were used without purification, and most reactions were carried out under argon. Silica gel used for flash chromatography was 230–400 mesh ASTM, purchased from Scientific Products while preparative plates (1000µ) and analytical plates were purchased from Analtech.

C-28 thioxene, substituted N-phenyl oxazine and thioxene attached to 9,10-bis(phenylethynyl) anthracene (BPEA) were prepared as described below. 2-Chloro 9,10-bis (phenylethynyl) anthracene (1-Cl-BPEA) and rubrene (5,6, 11,12-tetraphenyl naphthacene) were purchased from Aldrich Chemical Co. Rubrene was recrystallized from methylene chloride and stored at 4° C. in a brown bottle prior to use. Silicon phthalocyanine was prepared as described below and phthalocyanine tetrasulfonates was obtained from Ultra Diagnostics, Inc. Carboxylate-modified polystyrene (latex) particles were purchased from Seradyn, Inc. The particles were 203±4.0 nM. The carboxyl parking area was 49.5 angstroms squared (0.09 milliequivalents/g). Solids were 10% (100 mg/ml).

2-ethoxyethanol was from Aldrich Chemical Co. and was redistilled under vacuum. Sodium hydroxide was 0.1 N. Isopropanol was from Aldrich Chemical Co.

Unless otherwise indicated, oligonucleotides used in the following examples were prepared by synthesis using an automated synthesizer and were purified by gel electrophoresis or HPLC.

The following abbreviations have the meanings set forth below:

Tris HCl—Tris(hydroxymethyl)aminomethane-HCl (a 10×solution) from BioWhittaker, Walkersville, Md.

DTT—dithiothreitol from Sigma Chemical Company, St. Louis, Mo.

HPLC—high performance liquid chromatography.

DPP—4,7-diphenylphenanthroline from Aldrich Chemical Company, Milwaukee Wis.

BSA—bovine serum albumin from Sigma Chemical Company, St. Louis Mo.

ELISA—enzyme linked immunosorbent assay as described in "Enzyme-Immunoassay," Edward T. Maggio, CRC Press, Inc., Boca Raton, Fla. (1980)

bp—base pairs ddc—dideoxycytidine g—grams mmol—millimolar

DMF—dimethyl formamide

THF—tetrahydrofuran

LSIMS—fast ion bombardment mass spectroscopy

NMR—nuclear magnetic resonance spectroscopy

TMSCl—tetramethylsilylchloride

EDAC—1-ethyl-3-(3-dimethylaminopropyl)-carbodiimide hydrochloride.

MES—2-(N-morpholino)ethane sulfonic acid.

SPDP—N-succinimidyl 3-(2-pyridylthio)-propionate.

Sulfo-SMCC—N-sulfosuccinimidyl-4-(N-maleimidomethyl)cyclohexane-1-carboxylate.

TCEP—tris-carboxyethyl phosphine.

PREPARATION OF REAGENTS

C-28 Thioxene

To a solution of 4-bromoaniline (30 g, 174 mmol) in dry DMF (200 mL) was added 1-bromotetradecane (89.3 mL, 366 mmol) and N,N-diisopropylethylamine (62.2 mL, 357 mmol). The reaction solution was heated at 90° C. for 16 hr under argon before being cooled to room temperature. To this reaction solution was again added 1-bromotetradecane (45 mL, 184 mmol) and N,N-diisopropylethylamine (31 mL, 178 mmol) and the reaction mixture was heated at 90° C. for another 15 hr. After cooling, the reaction solution was concentrated in vacuo and the residue was diluted with $CH_2Cl_2$ (400 mL). The $CH_2Cl_2$ solution was washed with 1 N aqueous NaOH (2×), $H_2O$, and brine, was dried over $Na_2SO_4$ and was concentrated in vacuo to yield a dark brown oil (about 110 g). Preparative column chromatography on silica gel by a Waters 500 Prep LC system eluting with hexane afforded a yellow oil that contained mainly the product (4-bromo-N,N-di-($C_{14}H_{29}$)-aniline) along with a minor component 1-bromotetradecane. The latter compound was removed from the mixture by vacuum distillation (bp 105–110° C., 0.6 mm) to leave 50.2 g (51%) of the product as a brown oil. To a mixture of magnesium turnings (9.60 g, 395 mmol) in dry THF (30 mL) under argon was added dropwise a solution of the above substituted aniline product (44.7 g, 79 mmol) in THF (250 mL). A few crystals of iodine were added to initiate the formation of the Grignard reagent. When the reaction mixture became warm and began to reflux, the addition rate was regulated to maintain a gentle reflux. After addition was complete, the mixture was heated at reflux for an additional hour. The cooled supernatant solution was transferred via cannula to an addition funnel and added dropwise (over 2.5 hr) to a solution of phenylglyoxal (11.7 g, 87 mmol) in THF (300 mL) at −30° C. under argon. The reaction mixture was gradually warmed to 0° C. over 1 hr and stirred for another 30 min. The resulting mixture was poured into a mixture of ice water (800 mL) and ethyl acetate (250 mL). The organic phase was separated and the aqueous phase was extracted with ethyl acetate (3×). The combined organic phases were washed with $H_2O$ (2×), brine and were dried over $MgSO_4$. Evaporation of the solvent gave 48.8 g of the crude product as a dark green oily liquid. Flash column chromatography of this liquid (gradient elution with hexane, 1.5:98.5, 3:97, 5:95 ethyl acetate:hexane) afforded 24.7 g (50%) of the benzoin product (LSIMS ($C_{42}H_{69}NO_2$): [M-H]$^+$618.6, $^1$H NMR (250 MHz, $CDCl_3$) was consistent with the expected benzoin product. To a solution of the benzoin product from above (24.7 g, 40 mmol) in dry toluene (500 mL) was added sequentially 2-mercaptoethanol (25 g, 320 mmol) and TMSCl (100 mL, 788 mmol). The reaction solution was heated at reflux for 23 hr under argon before being cooled to room temperature. To this was added additional TMSCl (50 mL, 394 mmol); and the reaction solution was heated at reflux for another 3 hr. The resulting solution was cooled, was made basic with cold 2.5N aqueous NaOH and was extracted with $CH_2Cl_2$ (3×). The combined organic layers were washed with saturated aqueous $NaHCO_3$ (2×) and brine, was dried over $Na_2SO_4$ and was concentrated in vacuo to give a brown oily liquid. Preparative column chromatography on silica gel by using a Waters 500 Prep LC system (gradient elution with hexane, 1:99, 2:98 ethyl acetate:hexane) provided 15.5 g (60%) of the C-28 thioxene as an orange-yellow oil (LSIMS ($C_{44}H_{71}NOS$): [M-H]$^+$661.6, $^1$H NMR (250 MHz, $CDCl_3$) was consistent with the expected C-28 thioxene product 2-(4-(N,N-di-($C_{14}H_{29}$)-anilino)-3-phenyl thioxene.

Silicon Tetra-t-butyl Phthalocyanine:

Sodium metal, freshly cut (5.0 g, 208 mmol), was added to 300 mL of anhydrous methanol in a two-liter, 3-necked flask equipped with a magnetic stirrer, reflux condenser, a drying tube and a gas bubbler. After the sodium was completely dissolved, 4-t-butyl-1,2-dicyanobenzene (38.64 g, 210 mmol, from TCI Chemicals, Portland Oreg.) was added using a funnel. The mixture became clear and the temperature increased to about 50° C. At this point a continuous stream of anhydrous ammonia gas was introduced through the glass bubbler into the reaction mixture for 1 hr. The reaction mixture was then heated under reflux for 4 hr. while the stream of ammonia gas continued during the course of the reaction, as solid started to precipitate. The resulting suspension was evaporated to dryness (house vacuum) and the residue was suspended in water (400 mL) and filtered. The solid was dried (60° C., house vacuum, $P_2O_5$). The yield of the product (1,3-diiminoisoindoline, 42.2 g) was almost quantitative. This material was used for the next step without further purification. To a one-liter, three-necked flask equipped with a condenser and a drying tube was added the above product (18 g, 89 mmol) and quinoline (200 mL, Aldrich Chemical Company, St. Louis Mo.). Silicon tetrachloride (11 mL, 95 mmol, Aldrich Chemical Company) was added with a syringe to the stirred solution over a period of 10 minutes. After the addition was completed, the reaction mixture was heated to 180–185° C. in an oil bath for 1 hr. The reaction was allowed to cool to room temperature and concentrated HCl was carefully added to acidify the reaction mixture (pH 5–6). The dark brown reaction mixture was cooled and filtered. The solid was washed with 100 mL of water and dried (house vacuum, 60° C., $P_2O_5$). The solid material was placed in a 1-liter, round bottom flask and concentrated sulfuric acid (500 mL) was added with stirring. The mixture was stirred for 4 hr. at 60° C. and was then carefully diluted with crushed ice (2000 g). The resulting mixture was filtered and the solid was washed with 100 mL of water and dried. The dark blue solid was transferred to a 1-liter, round bottom flask, concentrated ammonia (500 mL) was added, and the mixture was heated and stirred under reflux for 2 hr., was cooled to room temperature and was filtered. The solid was washed with 50 mL of water and dried under vacuum (house vacuum, 60° C., $P_2O_5$) to give 12 g of product silicon tetra-t-butyl phthalocyanine as a dark blue solid. 3-picoline (12 g, from Aldrich Chemical Company), tri-n-butyl amine (anhydrous, 40 mL) and tri-n-hexyl chlorosilane (11.5 g) were added to 12 g of the above product in a one-liter, three-necked flask, equipped with a magnetic stirrer and a reflux condenser. The mixture was heated under reflux for 1.5 hr. and then cooled to room temperature. The picoline was distilled off under high vacuum (oil pump at about 1 mm Hg) to dryness. The residue was dissolved in $CH_2Cl_2$ and purified using a silica gel column (hexane) to give 10 g of pure product di-(tri-n-hexylsilyl)-silicon tetra-t-butyl phthalocyanine as a dark blue solid. (LSIMS: $[M-H]^+$ 1364.2, absorption spectra: methanol: 674 nm ($\epsilon$180,000): toluene 678 nm, $^1$H NMR (250 MHz, $CDCl_3$): $\delta$ −2.4(m, 12H), −1.3(m, 12H), 0.2–0.9 (m, 54H), 1.8(s, 36H), 8.3(d, 4H) and 9.6 (m, 8H) was consistent with the above expected product.

Hydroxypropylaminodextran

Hydroxypropylaminodextran ($1NH_2$/7 glucose) was prepared by dissolving Dextran T-500 (Pharmacia, Uppsala, Sweden) (50 g) in 150 mL of $H_2O$ in a 3-neck round-bottom flask equipped with mechanical stirrer and dropping funnel. To the above solution was added 18.8 g of Zn ($BF_4$)$_2$ and the temperature was brought to 87° C. with a hot water bath. Epichlorohydrin (350 mL) was added dropwise with stirring over about 30 min while the temperature was maintained at 87–88° C. The mixture was stirred for 4 hr while the temperature was maintained between 80° C. and 95° C., then the mixture was cooled to room temperature. Chlorodextran product was precipitated by pouring slowly into 3L of methanol with vigorous stirring, recovered by filtration and dried overnight in a vacuum oven.

The chlorodextran product was dissolved in 200 mL of water and added to 2L of concentrated aqueous ammonia (36%). This solution was stirred for 4 days at room temperature, then concentrated to about 190 mL on a rotary evaporator. The concentrate was divided into two equal batches, and each batch was precipitated by pouring slowly into 2L of rapidly stirring methanol. The final product was recovered by filtration and dried under vacuum.

Hydroxypropylaminodextran ($1NH_2$/7 glucose), prepared above, was dissolved in 50 mM MOPS, pH 7.2, at 12.5 mg/mL. The solution was stirred for 8 hr at room temperature, stored under refrigeration and centrifuged for 45 min at 15,000 rpm in a Sorvall RC-5B centrifuge immediately before use to remove a trace of solid material. To 10 mL of this solution was added 23.1 mg of Sulfo-SMCC in 1 mL of water. This mixture was incubated for 1 hr at room temperature and used without further purification.

N-Phenyl Oxazine (NPhe):

The N-phenyl oxazine was prepared by a procedure similar to that described in U.S. Pat. No. 5,578,498 (Singh, et al.) for the preparation of compound 16. The relevant disclosure of the above patent is incorporated herein by reference.

Thioxene Attached to 9,10-bis(Phenylethynyl) Anthracene:

To a 250 mL, 3-necked round bottom flask was added 62 g of N-methyl aniline (0.58 mole) and 62 g of ethyl 5-bromomovalerate (0.29 mole). The reaction mixture was heated to 100° C. for 16 hours with stirring. The brown reaction mixture was cooled to room temperature and poured into 100 mL of ethyl acetate. The ethyl acetate solution was washed with 20% sodium hydroxide (3×100 m.). The aqueous layer was extracted with 50 mL of ethyl acetate. The combined ethyl acetate solution was dried over sodium sulfate (50 g). The sodium sulfate was filtered through a glass funnel equipped with a cotton plug and the filtrate was concentrated under reduced pressure (30 mm Hg 40° C. rotavap). The brown residue was distilled under high vacuum (130–137° C., 0.5 mm Hg) to yield 60 g of the product, ethyl 5-methylanilinopentanoate, (86%) as a colorless liquid. $^1$H NMR ($CDCl_3$, 250 MHz): $\delta$ 1.3 (t, 3H), 1.65 (m, 4H), 2.3 (t, 2H), 2.8 (s, 3H), 3.3 (t, 2H), 4.2 (q, 2H), 6.65 (d, 2H), 7.2 (m, 3H).

A 3-necked, bound bottom flask was placed on an ice bath on a magnetic stirrer. Dimethylformamide (DMF) (8.8 g) was added and stirred until the temperature dropped to 4° C., $POCl_3$ (5.06 g) was added dropwise from the dropping funnel over a period of 10 minutes. After the addition, the reaction was stirred at 4° C. _for 10 minutes. Ethyl 5-methylanilinopentanoate prepared as described above (3.76 g) was added rapidly in less than 1 minute and the reaction was heated to 100° C. _for 1 hour. The reaction mixture was poured into ice and neutralized with 20% sodium hydroxide. The mixture was extracted with ethyl acetate (3×50 mL). The combined ethyl acetate solution was dried over sodium sulfate (50 g). The sodium sulfate was filtered through a glass funnel equipped with a cotton plug and the filtrate was concentrated under reduced pressure (30mm Hg, 40° C. rotavap). The residue was chromatographed on a silica gel column ($CH_2Cl_2$ to $CH_2Cl_2$:EtOAc 9:2) to give pure product, 4-(4-carboxybutyl) methylaminobenzaldehyde ethyl ester, as a yellow liquid.

$^1$H NMR ($CDCl_3$, 250 MHz): $\delta$ 1.2 (t, 2H), 1.6 (m, 4H), 2.3 (t, 2H), 2.9 (s, 3H), 3.3 (t, 2H), 4.1 (q, 2H), 6.6 (d, 2H), 7.6 (d, 2H), 9.7(s, 1 H).

To a 250-ml, 3-necked, round bottom flask equipped with a water condenser, a mechanical stirrer, and a thermometer was added 50 g of 4-(4-carboxybutyl) methylaminobenzaldehyde ethyl ester prepared as described above (20 mmol) and 2 g of potassium cyanide in 60% ethanol under argon. The reaction mixture was placed in an oil bath and refluxed. To the refluxing reaction mixture 2.15 g of benzaldehyde (20 mmol) in 20 ml of ethanol was added during 90 minutes. The reaction mixture was refluxed for 15 minutes more and extracted with ethyl acetate (3×50 mL). The combined ethyl acetate solution was dried over sodium sulfate (50 g). The sodium sulfate was filtered through a glass funnel equipped with a cotton plug, and the filtrate was concentrated under reduced pressure (30 mm Hg, 40° C. rotovap). The crude reaction mixture was incubated overnight at room temperature and then poured into a mixture of 150 mL of saturated aqueous sodium bicarbonate and 50 mL of methylene chloride. The organic layer was separated and washed with 100 mL of saturated sodium bicarbonate solution. The combined aqueous layer was extracted with 75 mL of $CH_2Cl_2$. The combined organic solution was dried over sodium sulfate (50 g), filtered through a glass funnel equipped with a cotton plug, and the filtrate was concentrated under reduced pressure (30 mm Hg, 40° C. rotovap). The product was purified on preparative TLC (hexane: ethyl acetate 5:1) to yield 2.2 g of the ethyl ester of α-hydroxy-α-phenyl-4-[(4-carboxybutyl)-methylamino] acetophenone.

$^1$H NMR ($CDCl_3$, 250 MHz): δ 1.3 (t, 3H), 1.6 (m, 4H), 2.4 (t, 2H), 2.9 (s, 3H), 3.3 (t, 2H), 4.1 (q, 2H), 4.8 (d, 1H), 5.8 (d, 1H), 6.5 (d, 2H) 7.3 (m, 5H), 7.8 (d, 2H).

To a stirred solution of the ethyl ester of α-hydroxy-α-phenyl-4-[(4-carboxybutyl)-methylamino] acetophenone (2.5 mmol) in 50 mL of dry toluene, 1.2 mL of thioethanol (15 mmol) was added, followed by 2.5 mL of TMSCl. The reaction mixture was refluxed in an oil bath under argon for 24 hours, allowed to come to room temperature and poured into 150 mL of saturated aqueous sodium bicarbonate solution. The combined aqueous layer was extracted with 75 mL of $CH_2Cl_2$. The combined organic solution was dried over sodium sulfate (50 g), filtered and concentrated under reduced pressure. The product was purified on a silica gel column ($CH_2Cl_2$: ethyl acetate 9:1) to yield 1.2 g of thioxene product (ethyl 5-methylaminopentanoate, amide with 2-[4-carboxybutyl)methylaminophenyl]-3-phenyl-5,6-dihydrothioxene) as a pale yellow oil.

Synthesis of Thioxene-Carboxcylic Acid:

To a stirred solution of 500 mg of the ethyl ester of 2-[4-carboxybutyl)methylaminophenyl]-3-phenyl-5,6-dihydrothioxene, prepared from the amide above by standard esterification methods, in 20 mL of THF, 10 ml of 2.0N sodium hydroxide was added. The reaction mixture was stirred under argon for 24 hours. The reaction mixture was neutralized with minimum amount of 1.0N HCl and the organic portion extracted into 50 mL of ethyl acetate. The organic layer was dried over 1.0 g of sodium sulfate and evaporated. The product, 2-[4-(carboxybutyl) methylaminophenyl]-3-phenyl-5,6-dihydrothioxene, was used as is for the next step.

Preparation of Thioxene-Phenanthrene

To a stirred solution of the thioxene carboxylic acid (120 mg, 0.3 mmol) in 20 ml of dry THF in a 50 mL round bottom flask equipped with a magnetic stirrer and an argon inlet tube was added carbonyl diimidazole (64 mg, 0.4) and 20 mg of dimethylamino pyridine. The reaction mixture was stirred at room temperature for 2 hours. The amino phenanthrene (160 mg, 0.5 mmol) was added to the reaction mixture in 2.0 mL of dry THF. The reaction mixture was stirred at room temperature for 16 hours. The reaction mixture was worked up as described in the thioxene preparation. The product was purified on preparative TLC (ethyl acetate: hexane 50:50) to yield 80 mg of a white waxy solid.

$^1$H NMR ($CDCl_3$: d, 0.7 (t,3H), 1.3 (m, 12H), 2.2 (t, 2H), 2.7 (t, 2H), 2.8 (s, 3H), 3.3 (m, 4H), 4.3 (s, 2H), 4.3 (s, 2H), 4.5 (t, 2H), 6.5 (d, 2H), 7.2 (m, 7H), 7.7 (m, 6H), 8.2 (d, d, 2H), and 8.7 (d, d, 2H). Mass Spectrum (CI: m/e): M$^+$ 684.

Synthesis of Thioxene-BPEA:

To 120 mg of 2-[4-(carboxybutyl)methylaminophenyl]-3-phenyl-5,6-dihydrothioxene prepared as described above (0.5 mmol) in 5.0 mL of THF was cooled in an ice bath for 30 minutes. 5.0 mL of oxalyl chloride was added to the cooled solution. The reaction mixture was stirred at 4° C. for 3 hours. Oxalyl chloride was evaporated on the rotovap under reduced pressure to give the acid chloride of 2-[4-(carboxybutyl)methylaminophenyl]-3-phenyl-5,6-dihydrothioxene. 2-Amino 9,10-bis-phenylethynyl anthracene (1.0 mmol) in 25 mL of dry THF was added to the residue followed by 2 drops of triethyl amine. The heterogeneous reaction mixture was stirred at room temperature for 24 hours. The reaction mixture was worked up as described for thioxene-phenanthrene. The product, 2-amino-9,10-bis(phenylethynyl)anthracene amide of 2-[4-(carboxybutyl)methylaminophenyl]-3-phenyl-5,6-dihydrothioxene (compound 7 in Table 1) was purified on preparative TLC ($CH_2Cl_2$: hexane 9:1) to yield 150 mg of yellow glassy solid.

$^1$H NMR ($CDCl_3$, 250 MHz): δ 1.6 (m, 6H), 2.5 (t, 2H), 2.9 (s, 3H), 3.3 (d,d, 2H), 3.45 (t, 2H), 4.5 (d,d, 2H), 6.55 (d, 2H), 7.0 (d, 2H), 7.2 (m, 5H), 7.7 (m, 15H). Mass Spectrum (CI: m/e, relative intensity) M$^+$ 758 (100). Absorption Spectra (Toluene): 330 nM (ε: 13,000), 448 nm, 476 nm (ε: 32,000).

Particle Dyeing

Microgon setup:

A Microgon was assembled as described in the 'Minikros lab systems' manual, pages 8–10. A 0.1 micron module was used operated between about 5–10 psi. The Microgon apparatus was washed with ethanol (200 proof.

Setup of apparatus:

1. An oil bath was heated to 95° C.±3° C. A three-necked 1 liter roundbottom flask (rbf) equipped with a digital cafeama mechanical stirrer from the middle neck was immersed into the oil bath.

2. Addition of particles: 200 ml±5.0 ml of latex particles were added to the rbf by means of a measuring cylinder, which was washed with 2×30 ml of ethoxyethanol (ee) and the contents were transferred to the rbf. To the flask was added 20±5 ml of 0.1 N sodium hydroxide. The particles were stirred at 330 rpm per minute at 95° C. for 20 minutes.

3. Addition of C-28 thioxene: 3.6 grams of C-28 thioxene was dissolved in 85 ml of ethoxyethanol and the resulting solution was added to the particles dropwise over 85–100 minutes at a constant addition rate of approximately 1.0 ml per minute. The particles were stirred for 5 minutes and 6.0 ml of 0.1 N sodium hydroxide and 30 ml of deionized water were added over 10 minutes. The particles were stirred for 5 minutes.

4. Addition of 1-Cl-BPEA): 1 gram of 1-C1-BPEA was added to 155 ml of ee and gently heated at 95° C. to dissolve the 1-Cl-BPEA. The ethoxyethanol solution of 1-Cl-BPEA was added to the particles over 60–70 minutes. The particles were stirred for 5 minutes and 6.0 ml of 0.1 N sodium hydroxide and 12 ml of deionized water were added to the particles over 5 minutes. The particles were stirred for 10 minutes.

5. Addition of Rubrene: rubrene (recrystallized M.P. 328° C.–329° C., 480 mg) was dissolved in 200 ml of 1,2-dimethoxyethane and was then added with stirring to the above particles over 70–90 minutes. Rate of addition was 3.0 ml per minute. Next, 30 ml of 0.1 N sodium hydroxide and 120 ml of deionized water were added to the particles over 30 minutes and the medium was stirred for 10 minutes. The medium was cooled to 40° C. over 1 hour with stirring. The particles were subjected to filtration on a Microgon apparatus using a 43 micron (Tetko) filter (from Tetko Inc., Briarcliff Manor, N.Y.).

The particles were determined to have approximately 15% by weight of dyes incorporated therein and the concentration of the particles was 37 mg/ml. The size of the particles was 216 nm ±17 nm. The concentration of dyes was as follows: C-28 thioxene, approximately 100 mM; 1-Cl-BPEA, approximately 43 mM and rubrene, approximately 21.5 mM.

A similar procedure was used for particle dyeing with all the chemiluminescent compositions described in Table 1.

Oligonucleotide Bound Sensitizer Particles:

The oligonucleotide was immobilized on the surface of the above particles in the following manner. Aminodextran (500 mg) was partially maleimidated by reacting it with sulfo-SMCC (157 mg, 10 mL $H_2O$). The sulfo-SMCC was added to a solution of the aminodextran (in 40 mL, 0.05 M $Na_2HPO_4$, pH 7.5) and the resulting mixture was incubated for 1.5 hr. The reaction mixture was then dialyzed against MES/NaCl (2×2L, 10 mM MES, 10 mM NaCl, pH 6.0, 4° C.). The maleimidated dextran was centrifuged at 15,000 rpm for 15 minutes and the supernatant collected. The supernatant dextran solution (54 mL) was then treated with imidazole (7 mL of 1.0 M solution) in MES buffer (pH 6.0) and into this stirred solution was added the stained photosensitizer particles (10 mL of 10 mg/mL). After stirring for 10 minutes the suspension was treated with EDAC (7 mmol in 10 mM pH 6.0 MES) and the suspension stirred for 30 minutes. After this time, SurfactAmps® (Pierce Chemical Company) Tween-20 (10%, 0.780 mL) was added to the reaction mixture for a final concentration of 0.1%. The particles were then centrifuged at 15,000 rpm for 45 minutes and the supernatant discarded. The pellet was resuspended in MES/NaCl (pH 6.0, 10 mM, 100 mL) by sonication. Centrifugation at 15,000 rpm for 45 minutes, followed by pellet resuspension after discarding the supernatant, was performed twice. The maleimidated dextran photosensitizer particles were stored in water as a 10 mg/mL suspension.

Thiolated oligonucleotide (oligonucleotide bearing a 5'-bis(6-hydroxyethyldisulfide) group) (Oligos Etc.) was dissolved in water at a concentration of 0.49 mM. To 116 µL of this solution was added 8.3 µL of 3.5 M sodium acetate, pH 5.3 and 8.9 µL of tris(carboxyethyl)phosphine (20 mM). After 30 minutes incubation at room temperature, 548 µL of cold ethanol. Was added and the mixture was maintained at about 20° C. for 1.5 hour. The precipitated oligonucleotide was recovered by centrifugation for 2 min. at 15,000 rpm in an Eppendorf centrifuge, then dissolved in 37.5 µL of 5mM sodium phosphate, 2 mM EDTA, pH 6.

An aliquot of the maleimidated beads prepared above containing 22 mg beads was centrifuged for 30 min. at about 37,000 g, and the pellet was resuspended in 96 µL of 0.26 M NaCl, 0.05% Tween-20, 95 mM sodium phosphate, and 0.95 mM EDTA, pH7. The thiolated oligonucleotide was added and the mixture was maintained at 37° C. for 64 hours under argon. A 10 µL aliquot of sodium thioglycolate was added and incubation was continued for 2 hours at 37° C. Water was added to a total volume of 1 mL, and the beads were recovered by centrifugation, then resuspended in 5 mL of 0.1 M NaCl, 0.17 M glycine, 10 mg/mL BSA, 1 mM EDTA, 0.1% Tween-20, and 0.5 mg/mL Calf thymus DNA (Sigma Molecular Biology grade), pH 9.2. After three hours, the beads were recovered and washed three times by centrifugation, twice in buffer A and once in standard PCR buffer. The product was stored refrigerated in PCR buffer. Buffer A contained 0.1 M Tris base (J.T. Baker Chemical Co.), 0.3 M NaCl (Mallinckrodt), 25 mM EDTA $Na_2\ H_2O$ (Sigma Chemical Co.), 0.1% BSA (Sigma Chemical Co.), 0.1% dextran (Pharmacia), HBR-1 (Scantibodies), 0.05% Kathon and 0.01% gentamicin sulfate (GIBCO) prepared by dissolving and adjusting pH to 8.20 with concentrated HCl and made up to 10 L with distilled water.

A similar procedure was used for the preparation of oligonucleotide bound chemiluminescer particles.

The above procedure may be modified in a manner similar to that described by Ullman, et al., *Proc. Natl. Acad. Sci. USA* (1994) 91:5426–5427 at column 10 f page 5427.

Example 1

Target HIV RNA (obtained from Organon Teknika, Boxtel, Netherlands) was amplified by the isothermal NASBA amplification procedure. The NASBA Amplification Kit of Organon Teknika was employed. Target RNA, referred to below as WT) at various initial input (number of molecules per reaction) was amplified in the presence of reference RNA, at known number of molecules. The reference RNA molecules, referred to below as $Q_a$) were engineered (by Organon Teknika) to be homologous to the target RNA except for an internal sequence of 21 nucleotides. This sequence in the reference RNA was 63 nucleotides from the 3'-end thereof and was complementary to the sequence in the third oligonucleotide probe as set forth below. The corresponding sequence in the target RNA was complementary to the sequence in the second oligonucleotide probe as set forth below. A sequence in both the target and reference RNA that was 29 nucleotides from the 3' end was complementary to a sequence in the first oligonucleotide probe or common probe.

The above design of the reference RNA ensures amplification of the reference and target RNA by the same NASBA primers and enzyme at equal amplification efficiency for target and reference RNA. The sequence of the target and reference RNA was as described by the manufacturer in the *J. of Virological Methods* (1993) 43:177–188.

A homogenous chemiluminescence detection method as described above was used to generate signals for determination. Chemiluminescence signal was produced when a pair of probes became bound to the target RNA analyte, one of which was bound to a singlet oxygen-producing particle, the sensitizer particle, and the other of which was bound to a particle dyed with a specific acceptor dye. These probes are referred to herein as particle detection probes. The particle detection probes included a first oligonucleotide detection probe that comprised a sequence that was complementary to a sequence in the first oligonucleotide probe indicated by underlining in the sequence below. A particle with which a sensitizer was associated was attached at the 3'-end of the first oligonucleotide detection probe. A second oligonucleotide detection probe comprised a sequence that was complementary to a sequence in the second oligonucleotide probe indicated by underlining in the sequence below.

DPA dyed particles were attached at the 3'-end of the second oligonucleotide detection probe. A third oligonucleotide detection probe comprised a sequence that was complementary to a sequence in the third oligonucleotide probe indicated by underlining in the sequence below. N-PHE dyed particles were attached at the 3'-end of the third oligonucleotide detection probe. The particle detection probes became bound to the respective first, second or third oligonucleotide probes used in this example, where the binding was non-covalent and based on the hybridization of a sequence of the particle detection probes, to a complementary sequence in the respective first, second or third oligonucleotide probes, either a 3'- or 5'-oligonucleotide tail. Chemiluminescence signals produced by complexes of the common sensitizer particle, with each of the specific chemiluminescer particles, were specifically detected.

First oligonucleotide probe:

5'($\underline{dT}$)$_{20}$TGTTAAAAGAGACCATCAATGAGGA  3'
(SEQ ID NO:1)

Second oligonucleotide probe:

5'(<u>TACT</u>)₅GCTGCAGAATGGGATAGA3' (SEQ ID NO:2)

Third oligonucleotide probe:

5'GATGACAGTCGCATGCAG(<u>CTAT</u>)₅ 3' (SEQ ID NO:3)

All probes were 3'-amino blocked and gel-purified by the manufacturer, namely, Oligos Etc. The underlined portions of the probes represent the sequences of 20 nucleotides that are complementary to the particle detection probes.

The sequence of the particle detection probe which is bound to the sensitizer particles was dA$_{24}$ (SEQ ID NO: 4).

The sequence of the particle detection probe which is bound to the chemiluminescer particles dyed with N-PHE was 5'-(ATAG)₆ (SEQ ID NO: 5).

The sequence of the particle detection probe which is bound to the chemiluminescer particles dyed with DPA was 5'-(ATGA)₆ (SEQ ID NO: 6).

RNA amplification of the test and reference RNA was carried out in mixtures containing all probes, detection particles and amplification reagents. The amplification reagents used were provided by the manufacturer (Organon Teknika). The lyophilized NASBA reagent Accusphere™ was reconstituted as directed. The reagent mixture includes all primers, NTPs, MgCl$_2$ and buffer components. The target and reference RNA, the first, second and third oligonucleotide probes and corresponding particle detection probes were added to the reconstituted reaction mixture. The concentration of the first oligonucleotide probe was 25 nM and the concentration of the second and third oligonucleotide probes were at final concentration of 25 nM. The concentration of the particle detection probes were at final concentration of 1 μg per reaction. Target and reference RNA molecules, at known number of molecules, were added (2 μl) to the corresponding amplification tubes. The total volume of the initial reaction mixtures, including the target and reference RNA, was 15 μl. The mixtures were overlaid with 20 μl white, light mineral oil (Aldrich Chemical Co.) and incubated at 65° C. for 5 min. Following incubation at 41° C. for 10 min., the mixture of enzymes (5 μl from Organon Teknika) was added.

Following addition of the enzyme mixture, the amplification reactions were carried out by incubation at 41° C. for 60 min. The signals were read using the following program: Illumination for 0.1 sec. and read for 2.0 sec. (380–440 nm filter), followed by illumination for 0.5 sec., delay for 30 sec. and read for 10 sec. (550–660 nm filter). All measurements were carried out using a manual reader built in-house. This reader is similar to conventional readers except that it had a mechanism for fast filter change. The results are summarized in Table 2.

TABLE 2

| Target | Corrected signal | | Ratio | |
|---|---|---|---|---|
| WT/Qa | DPA (WT) | N-Phe* (Qa) | Input | Signal |
| 0/0 | | | | /1.89** |
| 100/0 | 34471 | −30 | | |
| 50/0 | 23321 | −14 | | |
| 0/100 | 47 | 22540 | | |
| 50/100 | 19240 | 13559 | 0.5 | 0.72 |
| 100/100 | 24875 | 12445 | 1 | 1.00 |
| 500/100 | 26787 | 2095 | 5 | 5.00 |
| 1000/100 | 36528 | 292 | 10 | 14.82 |

*Corrected N-Phe signal = [S-B$_{n-Phe}$ minus S-B$_{DPA}$] × 0.028 wherein S-B is Signal-Background. The correction factor 0.028 reflects 2.8% cross-over of DPA signal into the N-Phe signal channel.
**The ratio of corrected signal from test (WT) and reference (Qa) was divided by 1.89, to reflect the difference of chemiluminescence signal detection.

In summary, the above results demonstrate that the ratio of concentrations of the target RNA sequences can be measured by measuring the corrected ratio of the chemiluminescent signals.

Example 2

NASBA amplification and quantification of an HIV target in sample was carried out as described in Example 1. Known input amount of the test HIV target (WT) was mixed with known input amount of reference target, Qa. 2 μl of the mixture of targets was added to 13 μl of reaction mixture containing the primers, dNTPs and NTPs, the NASBA buffer, the three probes and the chemiluminescer beads and the photosensitizer beads. The oligonucleotide chemiluminescer beads were dyed with DPA, for the WT specific probe, and N-PHE, for the Qa specific probe. 1 μg of each of the chemiluminescer beads was used per assay. The reaction mixture contained 0.25 μg (per assay) of the sensitizer beads (specific for binding of the common probe). The following probes were used in the example: Oligonucleotide SEQ ID NO: 1 (OB-1 common probe) at 12.5 nM; SEQ ID NO: 7 (EF-4; specific for WT) at 25 nM; and SEQ ID NO: 8 (EF-7; specific for Qa) at 25 nM.

The oligonucleotides EF-4 and EF-7 were as follows:

5' GCTGCAGAATGGATAGA(<u>TACT</u>)₅ 3' SEQ ID NO: 7 (EF-4)

5' GCTGCAGACAGTGTAGATA (<u>CTAT</u>)₅ 3' SEQ ID NO: 8 (EF-7).

All sequences were blocked at the 3'-end by the manufacturer and gel purified. The nucleotide tails on the oligonucleotide probes were complementary to the 24 nucleotide sequence present on the oligonucleotide bound chemiluminescer particles.

20 μl of mineral oil was added to each reaction tube and the tubes were incubated at 65° C. for 5 minutes followed by incubation at 41° C. for 10 minutes. 5 μl of a mixture of the amplification enzymes was added to each reaction tube and amplification was carried out for 90 minutes at 41° C. The signals were read as follows: Three cycles of 1 sec illumination and 0.5 sec read, followed by 30 sec delay and 10 sec read.

The obtained signals for the DPA and N-PHE chemiluminescence were corrected as follows: The background signal was subtracted and the obtained signal was corrected using a correction factor calculated from signal obtained with the individual targets. This correction was required due to cross over of the signal from one chemiluminescence into the other. The results are shown in Table 3 below.

TABLE 3

| Input Number of target molecules WT/Qa | Corrected Signal WT | Corrected Signal Qa | Ratio Input | Ratio Calc. Signal WT/Qa/1.5 |
|---|---|---|---|---|
| 1e5/5e3 | 47404 | 1348 | 20 | 23.44 |
| 5e4/5e3 | 49879 | 3562 | 10 | 9.34 |
| 5e4/5e3 | 51865 | 5609 | 10 | 6.16 |
| 5e3/5e3 | 40364 | 26688 | 1 | 1.01 |
| 5e3/5e3 | 36936 | 24148 | 1 | 1.02 |
| 5e2/5e3 | 14846 | 56322 | 0.1 | 0.18 |
| 5e2/5e3 | 13187 | 55392 | 0.1 | 0.16 |
| 2.5e2/5e | 962 | 67457 | 0.05 | 0.01 |
| 0/0 | 0 | 0 | | |
| 5e3/0 | 49174 | 274 | | |
| 0/5e3 | 1 | 63622 | | |

The above data demonstrate that the test target (WT) can be quantified using the ratio of chemiluminescence signals as described.

The above discussion includes certain theories as to mechanisms involved in the present invention. These theories should not be construed to limit the present invention in any way, since it has been demonstrated that the present invention achieves the results described.

Although the foregoing invention has been described in some detail by way of illustration and example for purposes of clarity and understanding, it will be obvious that certain changes or modifications may be practiced within the scope of the appended claims.

What is claimed is:

1. A chemiluminescent composition comprising a matrix having associated therewith at least one chemiluminescent compound and at least two fluorescent compounds.

2. A chemiluminescent composition according to claim 1 comprising one chemiluminescent compound.

3. A chemiluminescent composition according to claim 1 wherein said chemiluminescent compound is an olefinic compound activatable by singlet oxygen.

4. A chemiluminescent composition according to claim 1 wherein said chemiluminescent compound is an olefinic compound selected from the group consisting of thioxenes, dihydrooxazines and dioxenes.

5. A chemiluminescent composition according to claim 1 wherein the at least two fluorescent compounds are selected from the group consisting of anthracenes, coumarins and naphthacenes.

6. A chemiluminescent composition according to claim 1 comprising two fluorescent compounds which are an anthracene and rubrene.

7. A chemiluminescent composition according to claim 6 wherein said anthracene is bisphenylethynylanthracene.

8. A chemiluminescent composition according to claim 1 wherein said matrix is a particle.

9. A chemiluminescent composition according to claim 1 wherein a member of a specific binding pair is associated with said matrix.

10. A chemiluminescent composition according to claim 1 wherein said matrix is a particle selected from the group consisting of latex particles, liposomes and oil droplets.

11. A kit comprising in packaged combination:

a) a chemiluminescent composition comprising a particle having associated therewith (1) at least one chemiluminescent compound and at least two fluorescent compounds and (2) a member of a specific binding pair (sbp), and b) a sensitizer.

12. A method for determining the presence or relative amount of a component in a medium, said method comprising:

a) providing in combination (1) a medium suspected of containing said component and (2) a chemiluminescent composition comprising a particle having associated therewith at least one chemiluminescent compound and at least two fluorescent compounds wherein luminescence emitted by said chemiluminescent composition is activated by electromagnetic radiation, b) activating said chemiluminescent compositions, and c) detecting the amount of luminescence generated by said chemiluminescent composition, the amount thereof being related to the amount of said component in said medium.

* * * * *